United States Patent
Tajima

(10) Patent No.: US 8,921,095 B2
(45) Date of Patent: *Dec. 30, 2014

(54) BIOLOGICAL MATERIAL FIXED CARRIER ENCLOSING TIP, BIOLOGICAL MATERIAL FIXED CARRIER TREATMENT APPARATUS, AND TREATMENT METHOD THEREOF

(75) Inventor: Hideji Tajima, Matsudo (JP)

(73) Assignee: Universal Bio Research Co., Ltd., Matsudo-Shi, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/570,332

(22) Filed: Aug. 9, 2012

(65) Prior Publication Data

US 2013/0032249 A1 Feb. 7, 2013

Related U.S. Application Data

(63) Continuation of application No. 11/792,835, filed as application No. PCT/JP2005/022775 on Dec. 12, 2005, now Pat. No. 8,263,390.

(30) Foreign Application Priority Data

Dec. 10, 2004 (JP) .................. 2004-359201

(51) Int. Cl.
  *C12M 1/34* (2006.01)
  *G01N 21/01* (2006.01)
  *B01L 3/00* (2006.01)
  *B01L 3/02* (2006.01)
  *G01N 35/10* (2006.01)

(52) U.S. Cl.
  CPC ............... *B01L 3/502* (2013.01); *B01L 3/0275* (2013.01); *G01N 35/10* (2013.01); *B01L 2200/0631* (2013.01); *B01L 2200/0647* (2013.01); *B01L 2300/0609* (2013.01); *B01L 2300/0636* (2013.01); *B01L 2300/12* (2013.01); *G01N 2035/1053* (2013.01)
  USPC .................. 435/287.2; 435/287.3; 435/288.7; 422/405; 422/524; 422/525

(58) Field of Classification Search
  USPC .......... 435/287.3, 288.6, 288.7; 422/524, 525
  See application file for complete search history.

(56) References Cited

U.S. PATENT DOCUMENTS 5,045,286 A 9/1991 Kitajima et al.
5,720,923 A 2/1998 Haff et al.
(Continued)

FOREIGN PATENT DOCUMENTS

EP 1359420 11/2003
EP 1464700 10/2004
(Continued)

OTHER PUBLICATIONS

U.S. Appl. No. 11/664,980, Sep. 28, 2006, Hideji Tajima et al.
(Continued)

*Primary Examiner* — William H Beisner
(74) *Attorney, Agent, or Firm* — Haynes and Boone, LLP

(57) ABSTRACT

A biological material fixed carrier enclosing tip, a biological material fixed carrier treatment apparatus, and a treatment method thereof. An object is to obviate attachment control and suction control for storing and retaining the carrier in the tip form vessel, to simplify complex reaction processes, and to make processing of the biological material fixed carrier to be easily executed as a result of a small-scale device configuration. The biological material fixed carrier enclosing tip comprises: a tip form vessel having an installation opening part that is installable to a nozzle, and a narrow tube that possesses an opening, through which fluid inflow and outflow is possible, that is narrower than the nozzle; a carrier in which a predetermined biological material is fixed or fixable, and has a size or a shape that is able to pass through the opening; and an enclosing section provided on the tip form vessel.

18 Claims, 10 Drawing Sheets

(56) References Cited

U.S. PATENT DOCUMENTS

| | | | |
|---|---|---|---|
| 5,844,686 A * | 12/1998 | Treptow et al. | 356/440 |
| 6,277,628 B1 | 8/2001 | Johann et al. | |
| 6,312,886 B1 | 11/2001 | Lee et al. | |
| 6,416,716 B1 | 7/2002 | Shukla et al. | |
| 6,461,808 B1 * | 10/2002 | Bodner et al. | 435/4 |
| 6,660,233 B1 | 12/2003 | Coassin et al. | |
| 7,369,241 B2 | 5/2008 | Tajima | |
| 8,263,390 B2 * | 9/2012 | Tajima | 435/287.2 |
| 2001/0019826 A1 | 9/2001 | Ammann | |
| 2002/0007054 A1 | 1/2002 | Sakurai et al. | |
| 2002/0090729 A1 | 7/2002 | Neeper et al. | |
| 2003/0064386 A1 | 4/2003 | Karaki et al. | |
| 2004/0114890 A1 | 6/2004 | Tajima | |
| 2004/0166504 A1 | 8/2004 | Rossier et al. | |
| 2005/0130325 A1 | 6/2005 | Oshida et al. | |
| 2006/0154270 A1 | 7/2006 | Tajima | |
| 2008/0193995 A1 | 8/2008 | Tajima | |

FOREIGN PATENT DOCUMENTS

| | | |
|---|---|---|
| JP | 03-181853 | 8/1991 |
| JP | 05-281243 | 10/1993 |
| JP | 05-506930 | 10/1993 |
| JP | 08-062225 | 3/1996 |
| JP | 09-262084 | 10/1997 |
| JP | 10-117764 | 5/1998 |
| JP | 10-323177 | 12/1998 |
| JP | 2000-241436 | 9/2000 |
| JP | 2000-346842 | 12/2000 |
| JP | 2001-002695 | 1/2001 |
| JP | 2001-074756 | 3/2001 |
| JP | 2001-002695 | 7/2001 |
| JP | 2001-509256 | 7/2001 |
| JP | 2002-102681 | 4/2002 |
| JP | 2002-513936 | 5/2002 |
| JP | 2002-189033 | 7/2002 |
| JP | 2002-191351 | 7/2002 |
| JP | 2003-107083 | 4/2003 |
| JP | 2003-531381 | 10/2003 |
| JP | 2003-339374 | 12/2003 |
| JP | 2004-033907 | 2/2004 |
| JP | 2004-061397 | 2/2004 |
| JP | 2004-294316 | 10/2004 |
| JP | 2004-359202 | 12/2004 |
| JP | 2005-003251 | 1/2005 |
| JP | 2005-030906 | 2/2005 |
| JP | 2005-278437 | 10/2005 |
| JP | 2006-24502 | 9/2006 |
| JP | 2006-24503 | 9/2006 |
| JP | 2006-024504 | 9/2006 |
| JP | 2006-24505 | 9/2006 |
| JP | 2006-24527 | 9/2006 |
| WO | WO 00/67893 | 11/2000 |
| WO | WO 03/004160 | 1/2003 |
| WO | WO 03/060115 | 7/2003 |
| WO | WO 2004068144 A1 * | 8/2004 |
| WO | WO 2006/038643 | 4/2006 |
| WO | WO 2006/062236 | 6/2006 |
| WO | WO 2006/073170 | 7/2006 |

OTHER PUBLICATIONS

U.S. Appl. No. 29/277,775, filed Mar. 9, 2007, Hideji Tajima.
U.S. Appl. No. 29/277,777, filed Mar. 9, 2007, Hideji Tajima.
U.S. Appl. No. 29/277,778, filed Mar. 9, 2007, Hideji Tajima.
U.S. Appl. No. 29/277,779, filed Mar. 9, 2007, Hideji Tajima.
U.S. Appl. No. 29/277,780, filed Mar. 9, 2007, Hideji Tajima.
U.S. Appl. No. 11/792,783, filed Jun. 8, 2007, Hideji Tajima.
U.S. Appl. No. 11/794,828, filed Jul. 3, 2007, Hideji Tajima.
International Searching Authority "Written Opinion," Jan. 24, 2006, 4 pages, International Serial No. PCT/JP2005/018419, Japanese Patent Office.
International Searching Authority "International Search Report," Jan. 24, 2006, 2 pages, International Serial No. PCT/JP2005/018419, Japanese Patent Office.
International Searching Authority "Written Opinion," Mar. 7, 2006, 5 pages, International Serial No. PCT/JP2005/022776, Japanese Patent Office.
International Searching Authority "International Search Report," Mar. 7, 2006, 4 pages, International Serial No. PCT/JP2005/022776, Japanese Patent Office.
International Search Report issued by the Japanese Patent Office, Feb. 28, 2006, in connection with PCT/JP2005/022775.
International Searching Authority "Written Opinion," Apr. 18, 2006, 8 pages, International Serial No. PCT/JP2006/300064, Japanese Patent Office.
International Searching Authority "International Search Report," Apr. 18, 2006, 4 pages, International Serial No. PCT/JP2006/300064, Japanese Patent Office.
International Preliminary Examination Authority, "International Preliminary Examination Report on Patentability," Sep. 20, 2006, 13 pages, International Serial No. PCT/JP2005/018419, Japanese Patent Office.
International Preliminary Examination Authority, "International Preliminary Examination Report on Patentability," Nov. 29, 2006, 8 pages, International Serial No. PCT/JP2005/022776, Japanese Patent Office.
International Preliminary Examination Authority "Written Opinion," Jan. 30, 2007, 6 pages, International Serial No. PCT/JP2006/300064, Japanese Patent Office.
International Preliminary Examiantion Authority, "International Preliminary Examination Report on Patentability," May 1, 2007, 11 pages, International Serial No. PCT/JP2006/300064, Japanese Patent Office.
Supplementary European Search Report, dated Oct. 28, 2011, by the European Patent Office in connection with EP Application No. EP 05814465 (2 pages).
Office Action dated Nov. 21, 2012, by the USPTO, in connection with U.S. Appl. No. 13/484,358.
Office Action dated Jun. 19, 2013, by the USPTO, in connection with U.S. Appl. No. 13/484,358.
Office Action dated Aug. 3, 2011, by the USPTO, in connection with U.S. Appl. No. 11/792,835.
Notice of Allowance dated May 10, 2012, by the USPTO, in connection with U.S. Appl. No. 11/792,835.
Office Action dated Sep. 26, 2013, by the USPTO, in connection with U.S. Appl. No. 13/484,358.
Office Action dated Dec. 9, 2013, by the USPTO, in connection with U.S. Appl. No. 13/917,159.

* cited by examiner

BIOLOGICAL MATERIAL FIXED CARRIER ENCLOSING TIP, BIOLOGICAL MATERIAL FIXED CARRIER TREATMENT APPARATUS, AND TREATMENT METHOD THEREOF

CROSS REFERENCE

This application is a Continuation of U.S. patent application Ser. No. 11/792,835, filed Apr. 4, 2008, which issued as U.S. Pat. No. 8,263,390 on Sep. 11, 2012, and which is a United States National Phase Application of International Patent Application Number PCT/JP2005/022775, filed Dec. 12, 2005, which claims priority to Japanese Patent Application Number 2004-359201, filed Dec. 10, 2004, the disclosures of which are incorporated herein by reference.

TECHNICAL FIELD

The present invention relates to a biological material fixed carrier enclosing tip, a biological material fixed carrier treatment apparatus, and a treatment method thereof.

BACKGROUND ART

Conventionally, in a case where a series of reaction processes using a plurality of reagents and materials is performed on a target material, which becomes the subject of examination, for example, the target material is stored in a test tube by bonding to a microcarrier, such as a bead. Thereafter, a variety of reagents, or the like, are injected into the test tube, the carrier is separated by some method, the carrier is moved to another vessel, and other reagents, or the like, are further injected, and processes such as heating are performed. For example, in a case where the carrier is a magnetic body, separation is performed by means of a magnetic field by attachment onto the inner wall of the test tube.

Furthermore, in regard to a process that performs examination of a target material by using a plane form carrier, such as a slide, fixed with, for example, a variety of oligonucleotides, the base sequence structure of the target material is examined by performing a series of reaction processes that, moves the carrier itself into a suspension in which the labeled target material is suspended, dispenses a variety of reagents into the carrier itself, moves the carrier itself into a cleaning solution, and moves the carrier to a measurement position of a measuring device in order to perform measurement of the emitted light.

In order to perform these processes, the separation of the carrier itself, and the transport of the carrier itself is necessary, and consequently, there is a problem in that there is concern in the processes being complex and time-consuming. Particularly, in regard to a case where these carriers themselves are transported, a large burden is placed on the user in a case where it is performed manually, and furthermore, there is also concern regarding cross-contamination. Moreover, a large scale device is necessary in a case where transport of the carrier itself is performed by means of a machine. Furthermore, in a case where separation of a non-magnetic carrier is performed, it is necessary to separate by means of the size and specific gravity of the carrier, and there is a problem in the process being complex and time-consuming.

On the other hand, there is a method in which a test tube or a plane form carrier is not used, in which the reaction process is performed using a pipette device comprising; a pipette tip provided with a liquid passage, in which passage of a liquid is possible, a nozzle to which the pipette tip is installed, a magnetic device that exerts a magnetic field to the liquid passage of the pipette tip, and a suction and discharge mechanism that suctions and discharges liquid within the pipette tip. According to this method, as a result of suctioning a suspension in which a plurality of magnetic particles, in which various materials are retained on the surface, are suspended, and exerting a magnetic field at the time of suctioning, the magnetic particles can be efficiently suctioned into the liquid passage of the pipette tip, and separation, or the like, can be performed, though since the magnetic particles are able to pass through the liquid passage, in order to retain the magnetic particles within the pipette tip, attachment onto the inner wall by applying a magnetic field is necessary. Consequently, in order to perform processing, there is a need to combine the suction and discharge control, attachment control by means of a magnetic field, and movement control of the pipette tip. Furthermore in regard to a case where the carrier is a non-magnetic particle, there is a problem in that separation can not be performed by the device (Patent Documents 1 to 3).

[Patent Document 1] Japanese Patent Publication No. 3115501
[Patent Document 2] International Patent Publication No. WO96/29602
[Patent Document 3] International Patent Publication No. WO97/44671

DISCLOSURE OF INVENTION

Problems to be Solved by the Invention

Consequently, a first object of the present invention is in providing: a biological material fixed carrier enclosing tip, wherein by making it possible to perform processing on a carrier in which the various materials are fixed or are fixable, while it is enclosed within a tip form vessel, attachment control and suction control for storing and retaining the carrier in the tip form vessel is made unnecessary, complex reaction processes are simplified, and processing is made to be easily executed as a result of a small-scale device configuration; a biological material fixed carrier treatment apparatus; and the method thereof.

A second object is in providing: a biological material fixed carrier enclosing tip, wherein by making it possible to perform the enclosing and the removal of a carrier in which the various materials are fixed or are fixable, through a separate route to the route that performs suction and discharge of fluid or a material that is present within the fluid, or in a separate process, then a process in which the carrier and the fluid is divided is made unnecessary, complex reaction processes are simplified, and processing is made to be easily executed as a result of a small-scale device configuration; a biological material fixed carrier treatment apparatus; and the method thereof.

A third object is in providing: a biological material fixed carrier enclosing tip, wherein processing can be made efficient, and the reliability of processing and certainty of processing can be increased by, in regard to a carrier in which the various materials are fixed or are fixable, making it able to be easily enclosed by the tip form vessel that stores the same, and making processing, such as fixed processing with respect to the carrier itself, easily executed by detachment from the tip form vessel; a biological material fixed carrier treatment apparatus; and the method thereof.

A fourth object is in providing: a biological material fixed carrier enclosing tip, in which the material of the carrier is not restricted to a magnetic body material, and furthermore, in regard to the shape and the size of the carrier, the only condition is that it is enclosable within the tip form vessel, and therefore, the breadth of selections with respect to the material, the shape, and the size, increases, and the optimal material for processing can be selected; a biological material fixed carrier treatment apparatus; and the method thereof.

A fifth object is in providing: a biological material fixed carrier enclosing tip, wherein by controlling the amount of suction and discharge, the speed, the position, the frequency, the time, the timing, or the like, automation in regard to consistent processing is made easy; a biological material fixed carrier treatment apparatus; and the method thereof.

Means for Solving the Problem

A first aspect of the invention is a biological material fixed carrier enclosing tip comprising: a tip form vessel having an installation opening part that is installable to a nozzle that performs suction and discharge of gas, and a narrow tube that possesses an opening, through which fluid inflow and outflow is possible by means of the suction and discharge of gas, that is narrower than the nozzle; a carrier in which a predetermined biological material is fixed or fixable in a plurality of different positions that are determined beforehand that are distinguishable from the exterior, and has a size or a shape that is able to pass through the opening; and an enclosing section provided on the tip form vessel that encloses the carrier within the narrow tube in a state where it is able to make contact with the fluid that has flown into the vessel from the opening.

Here, the "predetermined biological material" is a biopolymer, for example, genetic material such as nucleic acids, proteins, sugars, sugar chains, or peptides, or chemical materials including low molecular weight compounds, and the biological material is used for detecting the bonding of a receptor biological material that possesses bondability to the biological material as a ligand, capturing, separating, extraction, and the like. As the receptor, genetic material such as nucleic acids, proteins, sugar chains, peptides, or the like, that respectively possess bondability to genetic material such as nucleic acids, proteins, sugar chains, peptides, or the like, are appropriate. Furthermore, as the biological material, or a replacement for the biological material, the organism itself, such as cells, viruses, and plasmids, can be used.

"Fixed", for example, includes cases of physical adsorption or electrical interaction in addition to the cases of covalent bonding and chemical adsorption. Furthermore, the predetermined chemical material is fixed to the carrier; chemically, by physical adsorption, by a specific reaction with a binding material provided fixed in an appropriate area, or by another method. Moreover, the reaction ability or the bonding ability with the biological material may be increased by forming the carrier with a porous material, a corrugated material, or a fibrous material. In order to perform fixing, a functional group is expressed or generated in the carrier. Consequently, by hydrolyzing the peptide bonds possessed by, for example, silk, or the like, which comprises "polyamide type polymers", totally aromatic polyamides such as nylon (3-nylon, 6-nylon, 6,6-nylon, 6,10-nylon, 7-nylon, 12-nylon, or the like) and PPTA (polyparaphenylene terephthalamide), or heterocycle-containing aromatic polymers, the functional groups used for fixing the biological material is expressed or generated. Examples of functional groups that are bondable with the biological material include carboxyl groups —COOH, amino groups —NH$_2$, and the derivatives thereof. Here, the pore diameter suitable for fixing the biological material is, for example, several micrometers or less.

The "carrier" is storable in and extractable from the tip form vessel, and is a solid body possessing a size that is able to pass through the opening part of the narrow tube. Within the narrow tube, microamounts of liquid, for example, a volume from several microliters to several hundred microliters, is handled, and it is necessary for the entire surface of the carrier and the liquid to be able to make contact. Therefore, it is suitable for the space enclosed by the surface of the carrier enclosed within the narrow tube and the inner wall of the narrow tube to have a capacity that corresponds to the microamount.

Consequently, if the size of the opening of the narrow tube for simplifying the suction and discharge of the liquid quantity, and the size in which the carrier is able to outflow from the opening, is considered, and furthermore, if the situation that the biological material is fixable in a plurality of different positions that are determined beforehand that are distinguishable from the exterior is considered, it is preferable if the carrier is a one-dimensional carrier that has a length along the narrow tube, although it is small in the perpendicular direction to the narrow tube. Here, the "one-dimensional carrier" refers to a carrier in which the fixed positions or fixable positions of the biological material can be specified by a one-dimensional coordinate along the axial direction of the narrow tube.

The carrier is not necessarily restricted to a case where it comprises a single solid body, and it may also be a case where it comprises a plurality of solid bodies. Examples of the carrier include plurality of particle form carriers, which are arranged in the longitudinal direction of a narrow tube, a narrow and long linear form flexible carrier, a narrow and long linear form non-flexible carrier, and a rod-form carrier. For all of these, in a case where it does not have an enclosing section, it is able to pass through the opening.

The carrier is a solid body that is, for example, fixed such that it is arranged with a spacing, or is fixable, such that one or more types of the predetermined types of biological materials become a predetermined relationship to the predetermined positions. In that case, as a result of a solution containing a biological material that is labeled by a labeling material comprising a luminescent material, such as a fluorescent material in which there is the possibility of bonding with these biological materials, making contact with the carrier, the presence of bonding with these biological materials is measured by measuring the luminescence at each position, and as a result of this, the structure, the characteristics, and the presence of the target biological material can be analyzed.

Examples of the "enclosing section" include those in which a permeable porous member, a permeable hole member, or the like, which allows the fluid to pass but does not allow the carrier to pass, is provided as a separate body to the tip form vessel, those in which the tip form vessel itself, for example, by deforming or processing the walls of the tip form vessel, is provided, and those in which a separate member and a processed wall of the tip form vessel, or the like, have been combined. In addition, as one that is provided as a separate body to the tip form vessel but is movable, it may be unable to pass through the opening itself and be joined to the carrier. An example in which the tip form vessel itself is used is one in which a protrusion section that protrudes out to the central direction of the tube is provided for narrowing the narrow tube in a manner such that it is squeezed.

Amongst the enclosing section, in regard to the "permeable porous member", there is no need for it to be a filter that collects some material by adsorption, or the like. However, in a case where the enclosing section is a filter or a thin-film form filter, such as a membrane, not only is the outflow of the carrier from the opening and the installation opening part prevented, but a predetermined material can be collected. In a case where the enclosing section is provided as a separate body to the tip form vessel, a member that is formed in a thin-plate form or a thin-film form that is thin in the flow direction of the fluid, is used, or a permeable porous member with a large pore diameter with a condition that the carrier does not flow out, is used. Furthermore, in a case where the tip form vessel is processed and provided as the enclosing section, by making the opening portion large with a condition that the carrier does not flow out, the pressure necessary for suction and discharge can be reduced.

The "tip form vessel" is a vessel that has an installation opening part for a nozzle, and a narrow tube that possesses an opening for the inflow and outflow of fluid. The installation opening part is provided on the upper end, the opening is provided on the lower end, and it is preferable for the opening to be narrower than the installation opening part or the nozzle, and to be provided on the end of the narrow tube, which is insertable into various vessels. It is preferable for a storage section that communicates the installation opening part and the narrow tube, in which liquid is storable, to be provided. This is because they cannot be directly communicated since the narrow tube is formed narrower than the installation opening part. In regard to the storage section, it is preferable for it to have a wide tube that is formed wider than the narrow tube. In regard to the narrow tube, there is a case where it is provided as a single body with the storage section or the wide tube, and there is a case where it is detachably provided. In the case where it is detachably provided, the storage of the carrier within the narrow tube is simple. This wide tube and this narrow tube are not restricted to a case in which it has a typical dispensing tip form, which has a narrow diameter section that corresponds to the narrow tube, which communicates with the wide diameter section. For example, instead of a wide diameter section, it may have a quadratic prism shape, and instead of a thin diameter tube, it may be a square cylinder form tube. Furthermore, the inner diameter or the cross-sectional size of the narrow tube is smaller than the inner diameter of the nozzle that is installed to the installation opening part. It is preferable for the capacity of the narrow tube to have a range from several microliters to several hundred microliters.

In regard to the material of the tip form vessel, it is preferable for, at the very least, the narrow tube portion to be a translucent material in order to enable optical measurements to be performed. Examples of the material of the tip form vessel include resins such as polyethylene, polypropylene, polystyrene, and acrylic, glass, metals, and metal compounds. In regard to the size, for example, it is a size in which several microliters to several hundred microliters of liquid is storable in the narrow tube.

A second aspect of the invention is a biological material fixed carrier enclosing tip wherein the enclosing section has one or two or more carrier passage blocking members that are provided as separate bodies with respect to the tip form vessel, such that an interval between the installation opening part and the opening is partitioned, such that fluid is able to pass through, but the carrier is not able to pass through.

Here, the "carrier passage blocking member" is formed by a separate member to the tip form vessel. It may be one in which the wall of the tip form vessel, or the like, and a processed wall of the tip form vessel, or the like, is combined and used. In regard to the carrier passage blocking member, for example, fluid is able to pass through as a result of having a pierced hole or by forming a space between the inner wall face of the vessel, although the size of the pierced hole or the space is a size or a shape in which the carrier is not able to pass through. For example, it is a member that is provided such that it partitions the narrow tube in a wheel form, a cross form, a straight line form, a radial form, a mesh form, or a circular form, or it is a permeable porous member.

As an example in which the tip form vessel itself is used, there is one in which a protrusion section that protrudes out in the central direction of the tube is provided for narrowing the narrow tube in a manner such that it is squeezed. Furthermore, in regard to the enclosing section, there is one in which it is joined to the carrier.

In regard to number of carrier passage blocking members, in order to prevent both the outflow of the carrier from the opening and the outflow from the installation opening part, it is preferable for it to be provided at, at the very least, two sites such that the carrier is sandwiched from both the opening side and the installation opening part side.

Here, by using the permeable porous member, different carriers that have a larger size than the pore diameter can be commonly enclosed with certainty.

By providing the carrier passage blocking member, which is provided as a separate body, such that it is freely detachable, the enclosing and extraction of the carrier can be easily performed.

A third aspect of the invention is a biological material solid body enclosing tip wherein the enclosing section has a protrusion section in which a wall face of the tip form vessel is made to protrude out in the direction in which the interval between the installation opening part and the opening is partitioned.

Consequently, since the carrier is not provided as a separate body, and the enclosing section is provided by processing or deforming the tip form vessel, the carrier can be enclosed with certainty.

A fourth aspect of the invention is a biological material fixed carrier enclosing tip wherein the enclosing section has a joining section for passing fluid but preventing passage of the carrier, that is joined to the carrier and is installed to the tip form vessel.

By having a joining section, for example, a narrow and long shaped carrier can be enclosed within the tip form vessel such that it does not flow out from the opening, with certainty.

A fifth aspect of the invention is a biological material fixed carrier enclosing tip in which the entire wall of the tip form vessel, or a portion thereof, is formed by a conductive member that has a predetermined electrical resistance value.

Here, by providing the conductive member to the tip form vessel, heat generation can be induced by making a terminal that is connected to an electrical circuit provided on the exterior come into contact with the conductive member, and by flowing an electrical current through the conductive member, which has a predetermined resistance value. The resistance value is controlled by a control section mentioned below, based on the processing contents.

Here, as the "predetermined electrical resistance value", it is a value in which the heat generation that is necessary for the conductive member to achieve a temperature according to the object can be performed by flowing a fixed electrical current within the conductive member. For example, in terms of the surface resistance value, it is, for example, several hundred ohms to several ohms per unit area, and furthermore, the resistance value at which induction heating is made possible is, for example, several ohm cm or more. As the conductive thin film, for example, there is a case where it comprises a single type of material that has a predetermined electrical resistance, or there is a case where two or more types of materials that have different resistance values are joined, adhered, deposited, fused, welded, bonded, attached, or pasted. In the former case, the temperature depends on the magnitude of the electrical current value, which is the electromagnetic signal, and in the latter case, as a result of the Peltier effect, the temperature depends not only on the electrical current value but also the orientation of the current, and not only heating, but cooling also becomes possible.

Examples of the "conductive member" include metals, metallic compounds such as metal oxides, conductive materials such as alloys, semiconductors, metalloids, and conductive resins, a combination of these conductive materials with non-conductive materials such as ceramics, glass, and synthetic resins, or it may be a combination between conductive materials. For example, there are cases of aluminum, aluminum oxide, tin oxide, iron, an iron alloy, a nichrome alloy, and a member formed by two types of different conductive materials that have been bonded by means of bonding, welding, or joining. By flowing an electrical current to these members, or in the case of iron or an iron alloy, by applying a temporally oscillating magnetic field, these members can be inductively heated. In a case where two types of conductive materials have been joined, heating and cooling can be performed by means of the orientation of the electrical current.

Examples of the shape of the conductive member include a linear form, a thin-film form, a foil form, a film form, a thin plate form, a plate form, a long and narrow shape, and a layer form. The conductive member may be bonded, welded or deposited on a non-conductive member in order to reinforce the conductive member. The conductive member is controlled to a predetermined temperature by means of the "electromagnetic signal" (an electrical signal or a magnetic signal). Thermodynamic signals resulting from the application of heat or cold air are excluded from the electromagnetic signal.

In regard to the wall, the inner wall face thereof faces into the tip form vessel, the outer wall face thereof is on the exterior of the tip form vessel, and it is a tip form vessel wherein the interval between the inner and outer wall faces is integrally formed. That is to say, the portion of the wall that is sandwiched by the inner wall face and the outer wall face of the tip form vessel is, for example, a metal, a resin, or the like, or it is formed as a wall in a solid state in which these have been bonded such that they are not freely divided. Consequently, as the conductive member that has been formed as the entire wall or a portion of the wall, in a case where this has a conductive member that is freely separable from the wall, then for example, conductive members that simply only make contact with the wall, conductive members that are freely detachably installed to the wall by means of a screw, or the like, conductive members that are freely detachably provided with respect to a separate member that is installed to the wall by welding, or the like, and conductive members that are completely separated from the wall, are able to be divided, and are therefore excluded. Consequently, if the conductive member is provided such that the wall of the tip form vessel becomes approximately the thickness demanded as the wall of the tip form vessel, then the size of the tip form vessel and the scale of the entire device is controlled, and it can be handled without an awareness of the presence of the heating device.

A sixth aspect of the invention is a biological material fixed carrier enclosing tip wherein the carrier has a plurality of particle form carriers, and the enclosing section is provided such that it sandwiches the plurality of particle form carriers at, at the very least, two positions within the narrow tube in a state where they are serially arranged such that the order thereof becomes constant within the narrow tube, and the plurality of different positions determined beforehand are made to correspond to the plurality of particle form carriers that are arranged in a predetermined order.

Here, in regard to "arranging the particle form carriers in a single row such that the order thereof becomes constant", for example, the vessel is made to have a narrow tube that is larger than the outer diameter of the particle form carriers, and an inner diameter, or a length and a diameter, that is smaller than two times the outer diameter thereof.

Consequently, the particle form carriers, as locations in which the biological material is fixed or is fixable, can be identified according to the order of the particle form carriers. The outer diameter of such a particle form carrier is, for example, approximately 0.1 mm to 3 mm, and the narrow tube is made to have an inner diameter of approximately 0.2 mm to 6 mm. The particle form carrier is, for example, a porous body or a solid body in which a functional group that is able to bond to the biological material is generated or expressed at the surface, or a combination of both. For example, it is formed by a fibrous material such as rubber, silicone, cellulose or nylon, a resin, glass, or a metal.

Amongst the plurality of particle form carriers, a portion (including a plurality of carriers) may be used not for the fixing of the biological material but as a marker for indicating standard positions. Consequently, labeling is performed by, in regard to the carriers, the shape thereof, the size, a luminescent material such as a fluorescent material, a pigment, a dye, or the like.

A seventh aspect of the invention is a biological material fixed carrier enclosing tip wherein a particle form carrier arranged at, at the very least, one end within the plurality of particle form carriers, has concavities and convexities on the surface thereof.

Consequently, even if the enclosing section has circular pierced holes, the particle form carriers do not block the pierced holes and interrupt the flow of fluid.

An eighth aspect of the invention is a biological material fixed carrier enclosing tip wherein the carrier is a narrow and long shaped linear form flexible carrier, and the predetermined biological material is fixed or is fixable along the longitudinal direction of the linear form flexible carrier at positions determined beforehand that are identifiable from the exterior, and the enclosing section has a joining section which joins the linear form flexible carrier to the narrow tube at two points along the longitudinal direction of the linear form flexible carrier, which are separated by a predetermined distance, such that the fluid is passable.

Here, the "linear form flexible carrier" is, for example, a string form carrier, and the string form carrier is enclosed in the dispensing tip form vessel such that it does not become loose, by applying a tensile force along the longitudinal direction thereof. In regard to the width or the outer diameter of the string form carrier, for example, approximately 0.1 mm to 3 mm is suitable. The string form carrier is, for example, a porous body or a solid body in which a functional group that is able to bond to the biological material is generated or expressed at the surface, or a combination of both. For example, it is formed by a fibrous material such as rubber, silicone, cellulose or nylon, a resin, or a metal. It is preferable for this linear form flexible carrier to be provided such that it does not make contact with the narrow tube. Furthermore, it is preferable for the biological material to be fixed along the longitudinal direction of the carrier with a spacing.

A ninth aspect of the invention is a biological material fixed carrier enclosing tip wherein the carrier is a non-flexible narrow and long shaped linear form non-flexible carrier, the predetermined biological material is fixed or is fixable along the longitudinal direction of the linear form non-flexible carrier at positions determined beforehand that are identifiable from the exterior, and the enclosing section has a joining section which joins the linear form non-flexible carrier to the narrow tube such that the fluid is passable.

Here, in regard to the width or the outer diameter of the linear form non-flexible carrier, for example, approximately 0.1 mm to 3 mm is suitable. The linear form non-flexible carrier is, for example, a porous body or a solid body in which a functional group that is able to bond to the biological material is generated or expressed at the surface, or a combination of both. For example, it is formed by a fibrous material such as rubber, silicone, cellulose or nylon, a resin, or a metal. The joining section is made to join the linear form non-flexible carrier to the narrow tube at, at the very least, one point thereof.

A tenth aspect of the invention is a biological material fixed carrier enclosing tip wherein within the narrow tube in which the carrier is enclosed, the capacity of the space in which fluid is storable is approximately several microliters to several hundred microliters.

Here, the "space in which fluid is storable" generally refers to the space that is created between the surface of the carrier that is enclosed in the narrow tube and the inner wall face of the narrow tube.

By restricting the capacity of the narrow tube in this manner, even if a microamount of liquid, that is to say liquid of a volume of several microliters to several hundred microliters, has been suctioned into the narrow tube, the liquid can be evenly and uniformly made to make contact with the surface of the carrier. This microamount is, normally in biochemistry, particularly in the field of DNA, an amount of material that is easily extracted from an organism and easily handled. Furthermore, as the tip form vessel, a wide tube that communicates with the narrow tube can be provided in addition to the narrow tube, and for example, a variety of liquid quantities can be handled by making it a capacity that is several times to several tens of times the capacity of the narrow tube.

An eleventh aspect of the invention is a biological material fixed carrier treatment apparatus comprising: a nozzle head that has one or a plurality of consecutive nozzles that perform suction and discharge of gas; a suction and discharge mechanism that performs suction and discharge of gas via the nozzles; one or two or more biological material fixed carrier enclosing tips that are installed or are installable to the nozzles, in which a fixed carrier, to which biological material is fixable or is fixed, is enclosed; a stage to which a liquid storage section group, in which a variety of liquids are stored or are storable, is provided; a movement device that relatively moves the nozzle head with respect to the liquid storage section group; and a control section that controls the amount, the speed, the frequency, the time, or the position of the suction and discharge of the nozzles based on; the structure of the biological material fixed carrier enclosing tip, the material conditions comprising the type of biological material that is fixed to the carrier or is present within the fluid, the concentration, the amount of liquid, and the coordinate position containing the storage position of the liquid, and the processing contents.

Here, the "processing contents" are, for example, reaction, cleaning, transporting, dispensing, separating, extracting, heating, cooling, clarifying, measuring, mixing, deviating, elution, stirring, or the like, or a series of these processes that are combined according to a predetermined order or a predetermined time schedule according to a processing objective while including overlaps. "Time" includes the duration time or the timing of suction and discharge. By setting the duration time or the timing, intermittent, continuous or periodic setting of the suction and discharge is made possible.

In the case of "reaction" processing, for example, according to the material conditions, in regard to the vessel position in which the corresponding reagent is stored, a control in which; the suction and discharge that is determined by the conditions is performed at a predetermined speed, and suction and discharge is repeated at a liquid quantity of, for example, 80 percent of the capacity of the carrier enclosing region of the narrow tube, is performed. In regard to the frequency of the suction and discharge thereof, the determined control is performed according to the material conditions. In the case of "cleaning" processing, for example, according to the material conditions, in regard to the vessel position in which the cleaning solution is stored, a control in which; the suction and discharge that is determined according to the process is performed at a predetermined speed, and suction and discharge is repeated a predetermined number of times, is performed. In the same manner, control of the suction and discharge according to the process is performed. In regard to the "speed", for example, since in a case where the handled material is DNA, the size thereof is small compared to proteins, it is necessary to increase the speed in order to increase the encounterability between DNA. Furthermore, the speed differs depending on the contents of processing, and in the case of cleaning and stirring, the speed of the suction and discharge thereof is low compared to a case where the reaction process is performed.

The "structure of the biological material fixed carrier enclosing tip" also includes the shape of the tip, the position, the shape, and the characteristics of the enclosed carrier, the shape of the enclosing section, or the like. Determining the action of the suction and discharge according to the "type of the biological material" means that, for example, in a case where it is generally smaller than the size of proteins, such as in the manner of genetic material such as DNA, it is easier to handle if the handled liquid quantity is small, and the speed is fast. This is because the smaller the size, the encounterability generally becomes low. Here, the biological material fixed carrier enclosing tip comprises, for example; a tip form vessel that has an installation opening part that is installed to the nozzle, and a narrow tube that has an opening through which inflow and outflow of fluid is possible by means of the suction and discharge of the gas, a carrier, in which a predetermined biological material is fixed or is fixable at a plurality of different positions determined beforehand that are identifiable from the exterior, that has a size or a shape that is able to pass through the opening, and an enclosing section that is provided to the tip form vessel that encloses the carrier within the narrow tube in a state where it is able to make contact with the fluid that has flown into the narrow tube from the opening.

A twelfth aspect of the invention is a biological material fixed carrier treatment apparatus further comprising a light reception device that receives light from the carrier stored within the tip form vessel.

In regard to the light reception by means of the light reception device, there is a case where it is collectively performed with respect to a plurality of biological material fixed carrier enclosing tips that are installed to a nozzle head that has a plurality of consecutive nozzles, and there is a case where light reception is serially performed for each tip by means of the light reception device. In the latter case, it is performed by using a movement device that relatively moves between the light reception device and the vessel while relatively transporting the tip or the light reception device serially one at a time. In that case, since the measurement is performed by shifting the time, some kinds of reagents, for example, the PCR reaction solution in the previous process of PCR, in a case where extraction of DNA is performed, or a substrate solution to be injected in the case of chemiluminescence, need be dispensed immediately before reaction or a fixed time before reaction. Consequently, dispensing is not performed simultaneously, and it is preferable for dispensing to be performed by temporally shifting one at a time and providing a time difference. In a case where fluorescence is measured, a luminescent device that irradiates a predetermined excitation light into the vessel is further provided.

A thirteenth aspect of the invention is a biological material fixed carrier treatment apparatus wherein the capacity of a space in which liquid is storable within a narrow tube, in which the carrier is enclosed, is approximately several microliters to several hundred microliters.

Consequently, in regard to the liquid storage provided on the exterior of the biological material fixed carrier enclosing tip, the several microliters to several hundred microliters of liquid must be storable such that it is able to be suctioned into the narrow tube through the opening of the narrow tube.

A fourteenth aspect of the invention is a biological material fixed carrier storage device wherein a temperature raising and lowering body that raises and lowers the temperature as a result of a signal from the exterior is provided in the vicinity of, making contact with, or able to be in the vicinity of or making contact with, the outside of the narrow tube of the biological material fixed carrier enclosing tip. Here, the "temperature raising and lowering body" refers to a member or a device that is able to raise or lower the temperature thereof according to a signal from the exterior. The "signal" is, in a case where the temperature raising and lowering body is a conductive member, an electromagnetic signal, that is to say, a signal resulting from electricity or magnetism. It is also possible to detect the temperature resulting from the temperature raising and lowering body and generate the signal based on the temperature.

It is preferable for the temperature raising and lowering body to be relatively movably provided with respect to the biological material fixed carrier enclosing tip. Furthermore, in this case, the control section, in addition to control of the suction and discharge, consequently controls the temperature control based on the processing contents.

A fifteenth aspect of the invention is a biological material fixed carrier treatment apparatus wherein the nozzle head has a collective nozzle head in which a plurality of consecutive nozzles are arranged along the column direction and an individual nozzle head that has at least one nozzle, the suction and discharge mechanism has a collective suction and discharge mechanism that simultaneously performs suction and discharge of gas with respect to the plurality of consecutive nozzles of the collective nozzle head, and an individual suction and discharge mechanism that individually performs suction and discharge of gas with respect to each nozzle of the individual nozzle head, and the movement device has, a nozzle head movement device that relatively moves the collective nozzle head and the individual nozzle head in the row direction with respect to the liquid storage section group, and a transporting route that includes a column transporting route that is on the movement route of the collective nozzle head and along the column direction and a row transporting route that is on the movement route of the individual nozzle head and along the row direction, and has a queued route transporting device that transports a transport storage section, in which tips that have been detached from the collective nozzle head or liquid that has been discharged from the collective nozzle head are respectively storable, along the transporting route.

Here, there is no need for the "column direction" and "row direction" to necessarily be orthogonal such as in an X direction (horizontal direction) and a Y direction (vertical direction), and a case where they are oblique is acceptable. The collective nozzle head and the individual nozzle head may be individually movable. Furthermore, if the queued route transporting device has a row transporting route and a column transporting route on the movement route of the nozzle head, for example, it may be a case where it has a closed transporting route, such as a square shape or a polygonal shape, or it may be a case where it has an open transporting route. Here, the "transport storage section" is a portion that stores the tip or the liquid in the transporting device, and it is preferable if, at the very least, it has the same number of transport storage sections as the number of nozzles of the collective nozzle head.

A sixteenth aspect of the invention is a biological material fixed carrier treatment apparatus wherein the nozzle head has a plurality of consecutive collective nozzles and one individual nozzle arranged along the column direction, the suction and discharge mechanism simultaneously performs suction and discharge of gas with respect to the collective nozzles and the individual nozzle of the nozzle head, and the movement device has, a nozzle head movement device that relatively moves the nozzle head along the row direction with respect to a stage that has the liquid storage section group, and a transporting route that includes a column transporting route that is on the movement route of the collective nozzles and along the column direction and a row transporting route that is on the movement route of the individual nozzle and along the row direction, and has a queued route transporting device that transports a transport storage section, in which tip form vessels that have been detached from the collective nozzle or liquid that has been discharged from the collective nozzle head are respectively storable, along the transporting route.

A seventeenth aspect of the invention is a biological material fixed carrier treatment apparatus wherein a light reception device, which receives light within the tips or the tubes that have been detached, is provided at a predetermined position along the transporting route of the queued route transporting device.

An eighteenth aspect of the invention is a biological material fixed carrier treatment method comprising: a fixing step for fixing a predetermined biological material to a carrier such that it is associated with a predetermined position by a predetermined relationship; an enclosing step for storing the carrier, which is one that is able to pass through the opening, to which the biological material is fixed within a tip form vessel which has an installation opening part that is installable to one or a plurality of consecutive nozzles that perform suction and discharge of gas, and a narrow tube that has an opening, through which inflow and outflow of fluid is possible by means of the suction and discharge of gas, and is narrower than the nozzle, enclosing the carrier within the narrow tube in a state where it is able to make contact with the fluid that has flowed in from the opening to within the vessel by using an enclosing section, and installing to the nozzle at the installation opening part of the vessel; and a reaction step for moving a nozzle to which said tip form vessel has been installed to a predetermined liquid storage section, and bringing into contact and reacting the biological material fixed to the carrier and a solution stored in the liquid storage section by controlling the operation of suction and discharge, which comprises the amount of suction and discharge via the nozzle, the speed, the frequency, the time, or the location, based on the shape of the biological material fixed carrier enclosing tip, the shape of the carrier, the material conditions comprising the type of biological material that is fixed to the carrier or is present in the solution, the concentration, the amount of solution, or the position coordinate which includes the storage position of the solution, and the processing contents.

A nineteenth aspect of the invention is a biological material fixed carrier treatment method that, following the reaction step, has a light reception step for receiving light from the carrier stored within the tip form vessel.

A twentieth aspect of the invention is a biological material fixed carrier treatment method wherein the reaction step has a temperature raising and lowering step for raising and lowering the temperature within the narrow tube of the biological material fixed carrier enclosing tip.

A twenty-first aspect of the invention is a biological material fixed carrier treatment method wherein the fixing step fixes various types of biological materials (probe materials) to fixable particle form carriers by bonding the biological material to each type, the enclosing step includes a step for cleaning the enclosed particle form carriers by using a suitable solvent, and the reaction step has a step for performing suction and discharge of a liquid from the liquid storage section, in which a liquid containing the labeled target material is stored, at a predetermined speed and frequency, and a step for cleaning the particle form carriers by performing suction and discharge of a cleaning solution from the liquid storage section, in which a cleaning solution is stored, at a predetermined speed and frequency.

Effects of the Invention

According to the first aspect of the invention, the carrier is fixed or is fixable with various types of biological materials, and it becomes possible to perform processing while the carrier, which is able to flow out from the opening, is within the narrow tube. Consequently, adsorption control and suction control to the inner wall, which uses a magnetic force in order to retain the carrier in the narrow tube, is made unnecessary, the complex reaction process is simplified, and processing can be easily executed by a small-scale device configuration.

Furthermore, according to the present aspect of the invention, in regard to the carrier in which a variety of types of biological materials are fixed or are fixable, the enclosing and the removal thereof is performed by a separate route to the route in which suction and discharge of fluid, or the material that is suspended in the fluid, is performed. Consequently, a process for separating the fluid and the carrier is made unnecessary, the complex reaction process is simplified, and processing can be easily executed by a small-scale device configuration.

Moreover, according to the present aspect of the invention, by merely performing suction and discharge of fluid while enclosing the carrier within the narrow tube, and by moving the narrow tube, a variety of processes, for example, reaction, washing, temperature control, separation, stirring, dispensing, clarifying, isolation, elution, and extraction can be performed, and therefore, processing can be performed efficiently, quickly, and easily.

Furthermore, according to the present aspect of the invention, since the reaction with the biological material fixed to the carrier up until measurement can be performed while enclosed within the narrow tube, the target process can be performed consistently, without being manually handled, and automatically, and therefore, a process that has a high reliability can be performed with certainty. Moreover, by selecting the tip such that it has a shape that is suitable for the speed of the fluid and the liquid quantity to be handled, it can be made to handle a variety of processes. Therefore it has generality and diversity.

According to the second aspect of the invention, as the enclosing section, a carrier blocking member is provided as a separate body to the tip form vessel. Consequently, by installing the carrier blocking member to the tip form vessel, the carrier can be easily enclosed. Furthermore, by installing the carrier blocking member such that it is freely detachable, the tip form member can be reused, or it becomes possible to directly extract or collect the material adsorbed on the carrier.

According to the third aspect of the invention, as the enclosing section, a protrusion section, in which the wall face of the tip form vessel has been made to protrude, is provided. Consequently, as well as decreasing the number of components, and reducing the production cost, the carrier can be enclosed with certainty.

According to the fourth aspect of the invention, a joining section is provided as the enclosing section, the carrier is joined, and it can be installed to the tip form vessel with certainty.

According to the fifth aspect of the invention, by flowing an electrical current to a conductive member that is formed on the entire, or on a part of, the wall of the tip form vessel, and performing heat generation of the conductive member, and hence heating or cooling the carrier and the liquid stored in the tip form vessel, temperature control of the reaction can be performed.

Consequently, compared to a case where a heating device, such as a heater, is provided on the outside of the wall of the tip form vessel, since it is directly making contact with the inside of the tip form vessel, the reflection of heat by the wall is prevented, the heat can be more efficiently transmitted with respect to the inside of the tip form vessel, the thermal efficiency is high, and an accurate temperature control can be performed.

Furthermore, since the wall of the tip form vessel is formed by a conductive member, the thermal efficiency is high, it is not necessary to provide a heating device that is larger than necessary, such as a metallic block, to the outside of the tip form vessel, and it is sufficient to only provide the driving device to the exterior. Consequently, the structure of the exterior is simplified, and the entire device scale can be reduce.

Since an optical temperature raising and lowering body can be provided to the tip form vessels beforehand, it is not necessary to provide a heating device that satisfies a variety of conditions, to the exterior, and it has generality and diversity.

Since the conductive member directly makes contact with the inside of the tip form vessel, temperature control of the liquid can be performed with a high accuracy and faithfulness.

The time from applying the signal to the tip form vessel and the conductive member for heating or cooling with respect to the liquid until the liquid temperature becomes a uniform temperature distribution is shortened, and the process can be quickly and efficiently performed.

According to the sixth aspect of the invention, a plurality of particle form carriers are used as the carrier, and they are enclosed within the tip form vessel in a state where they are serially arranged such that the order thereof becomes constant. Consequently, by specifying the arrangement order of the particle form carriers, it becomes possible to specify the biological materials, and the specification of the biological material can be performed with certainty based on the arrangement order with a high reliability.

Since it is possible to divide each of the particle form carriers, then by collecting the particle form carriers in the same arrangement order, it becomes possible to extract or collect the biological materials for each carrier.

According to the seventh aspect of the invention, the particle form carrier arranged at, at the very least, one end within the plurality of particle form carriers stored within the narrow tube, has concavities and convexities on the surface thereof. Consequently, even if the enclosing section has circular pierced holes, the particle form carrier does not block the pierced holes and interrupt the flow of fluid, and the contact with the fluid is made certain.

According to the eighth aspect of the invention, an enclosing section that is joined to a flexible narrow and long shaped linear flexible carrier is used. Consequently, the outflow from the opening of the carrier is prevented, and it can be enclosed with certainty.

According to the ninth aspect of the invention, by using an enclosing section that is joined to a non-flexible narrow and long shaped linear non-flexible carrier, and by joining to the linear non-flexible carrier at, at the very least, one position, outflow from the opening of the carrier is prevented, and it can be enclosed with certainty.

According to the tenth aspect of the invention, within the narrow tube, by suppressing the capacity of the space formed between the surface of the carrier enclosed in the narrow tube and the inner wall face of the narrow tube, to the amount of liquid used for processing (microamount), the contact between the liquid suctioned into the narrow tube and the entire surface of the carrier is made possible, and handling with a high reliability with respect to the microamount of liquid is made possible.

In the eleventh aspect of the invention, the biological material fixed carrier enclosing tip, in which a carrier, to which a biological material is fixed or is fixable, is enclosed within the narrow tube, is installed to the nozzle, and the amount, the speed, the frequency, or the position of the suction and discharge with respect to the nozzle is controlled based on the material conditions, which comprise the shape of the tip thereof, the shape of the carrier, the type of the biological material that is fixed on the carrier or is to be suspended, the amount of liquid, and the coordinate position which includes the storage position of the liquid, and the processing conditions, which comprise the time and the temperature of incubation, or the processing contents.

Consequently, according to the present aspect of the invention, as well as using a biological material fixed carrier enclosing tip with a predetermined structure, by performing fine controls with respect to the suction and discharge, processes such as reaction, stirring and cleaning, on the biological material which is fixed or is fixable to the carrier that is enclosed within the tip, can be easily, consistently, quickly, and efficiently performed with a high reliability. Furthermore, according to the present aspect of the invention, by changing the contents of the control, a variety of processes can be handled, and therefore, it has generality and diversity.

According to the twelfth aspect of the invention or the nineteenth aspect of the invention, by receiving light from the carrier, processing up until measurement can be performed more consistently, quickly, and efficiently with a high reliability.

According to the thirteenth aspect of the invention or the twentieth aspect of the invention, within the narrow tube, in a state where the carrier has been enclosed, by suppressing the capacity of the space in which the fluid is storable to a microamount, the contact between the liquid suctioned into the narrow tube and the entire surface of the carrier is made possible, and a handling with a high reliability with respect to the microamount of liquid is made possible.

According to the fourteenth aspect of the invention, temperature control is performed on the narrow tube of the biological material fixed carrier enclosing tip, and consequently on the carrier enclosed therein, by approaching a temperature raising and lowering body from the exterior. Consequently, compared to a case where temperature control is performed and reaction with the carrier is performed by heating a vessel provided outside the tip, the reaction can be more efficiently performed with certainty.

According to the fifteenth aspect of the invention, the collective nozzle head and the individual nozzle head is simultaneously movable in the row direction, and a queued route transporting device having a transport route provided with the column transporting route and the row transporting route, is provided on the movement route of the collective nozzle head and the individual nozzle head. Consequently, as a result of the transporting device, it is processable by either the collective nozzle head or the individual nozzle head, a plurality of nozzles and a suction and discharge mechanism are not arranged in a queue form, and a variety of complex processes are made possible by a simple and compact structure using a small number of nozzles.

Furthermore, at the time the suction and discharge process is performed with respect to a plurality of processing subjects, in regard to the common processing items, by collectively performing processing using the collective nozzle head, and in regard to the processing items in which it is necessary to individually perform processing, by performing processing individually using the individual nozzle head, a variety of processes can be efficiently and quickly performed. In particular, in regard to a case where a measurement is performed individually, it is suitable for a case where a necessary reagent is added directly before the measurement thereof, or a case where a reagent with a need for maintaining a predetermined temperature is added directly before processing that is performed individually.

According to the sixteenth aspect of the invention, as well as demonstrating the same effects as the aforementioned fifteenth aspect of the invention, since suction and discharge of the collective nozzle and the individual nozzle can be further simultaneously performed with the same suction and discharge mechanism, the structure is simpler.

According to the seventeenth aspect of the invention, by providing a light reception device at, at the very least, one position on the transporting route of the queued route transporting device, processes that handle the nozzles that are processed with a plurality of consecutive nozzles, and serial measurement using a small number of light reception devices, can be performed. Consequently, the device can be simplified. In particular, since reagents that only become necessary directly before light reception by the light reception device, can be serially charged by the individual nozzle head directly before light reception, light reception can be performed efficiently with a high reliability.

According to the eighteenth aspect of the invention, the biological material fixed carrier enclosing tip, in which a carrier, to which a biological material is fixed or is fixable, is enclosed within the narrow tube, is installed to the nozzle, and the amount, the speed, the frequency, or the position of the suction and discharge with respect to the nozzle is controlled based on the material conditions, which comprise the shape of the tip thereof, the shape of the carrier, the type of the biological material that is fixed on the carrier or is to be suspended, the amount of liquid, and the coordinate position which includes the storage position of the liquid, and the processing conditions, which comprise the time and the temperature of incubation, or the processing contents. Consequently, according to the present aspect of the invention, as well as using a biological material fixed carrier enclosing tip with a predetermined structure, by performing fine controls with respect to the suction and discharge, processes such as reaction with the suctioned liquid, the stirring thereof, and cleaning, on the biological material which is fixed or is fixable to the carrier that is enclosed within the tip, can be easily, consistently, quickly, and efficiently performed with a high reliability. Furthermore, by changing the contents of the control, a variety of processes can be handled, and therefore, it has generality and diversity.

According to the twenty-first aspect of the present invention, since the biological material is made to bond to each particle form carrier, and each type, it does not distribute as a result of the dispensing process, and since fixing can be performed, the process is simplified.

BEST MODE FOR CARRYING OUT THE INVENTION

According to the present invention, as well providing an enclosing section to the tip form vessel and enclosing a biological material fixed carrier such that it becomes able to make contact with the fluid, by making the fixed positions measurable from the exterior, a consistent automation of a process from a sufficient reaction between the biological material and the biological material contained in the liquid that has flowed in until arriving at the measurement, is achieved.

Next, the embodiments of the present invention are explained based on the drawings. The explanation of the embodiments should in no way be interpreted as limiting the present invention unless particularly specified.

FIG. 1(*a*) shows a cross-sectional view of a biological material fixed carrier enclosing tip 11 according to a first embodiment of the present invention. The biological material fixed carrier enclosing tip 11 comprises a tip form vessel 12, which has a translucency, that has a wide tube 13 as a storage section in which the liquid is storable, and a narrow tube 15 that is formed narrower than the wide tube 13. The upper end of the wide tube 13 has an installation opening part 14 that is to be installed to a nozzle, which is not shown in the drawing, that performs suction and discharge of gas. An opening 16, through which fluid inflow and outflow is possible by means of the suction and discharge of gas, is provided on the end of the narrow tube 15.

A filter 20 is installed on the somewhat lower side of the installation opening part 14 of the wide tube 13, and it is possible for gas to pass therethrough. A thread form carrier 17 with a flexibility is stored in the narrow tube 15 in a state where a tensile force has been applied, and in a state where it has been linearly stretched along the central axis of the narrow tube 15 such that it does not make contact with the inner wall of the narrow tube 15. In regard to the thread form carrier 17, the top side thereof is installed by means of a centering member 18 that is installed by utilizing an approximately funnel form transitive section 15*a* from the wide tube 13 of the tip form vessel 12 to the narrow tube 15 and engaging thereto, and the bottom side thereof is installed by means of a centering member 19 that is installed by engaging the opening 16 of the tip form vessel 12. Consequently, the thread form carrier 17 is provided along the axis of the narrow tube 15.

As shown in FIG. 1(*b*), the centering member 18 has an engaging tube 22 that is formed such that it is tapered such that it engages the transitive section, and the engaging tube 22 has a plurality of supporting plates 22*a* that are formed in a radial form from an axle 21, to which the thread form carrier 17 is installed, that is formed along the central axis of the engaging tube 22. Furthermore, as shown in FIG. 1(*c*), the centering member 19 has, from a circularly formed flange 24, a plurality of supporting plates 24*a* that are installed to the flange 24, which are formed in a radial form from an axle 23, to which the thread form carrier 17 is installed, and which is formed along the central axis of the flange 24. Consequently, although the passage of fluid is possible through the centering members 18 and 19, it corresponds to a carrier passage blocking member of the enclosing section that encloses the thread form carrier 17 in the narrow tube 15, such that the thread form carrier 17 is not discharged from the opening 16.

Next, FIG. 1(*d*) shows a cross-sectional view of a biological material fixed carrier enclosing tip 25 according to a second embodiment of the present invention. In regard to the biological material fixed carrier enclosing tip 25, as well as using the aforementioned tip form vessel 12, it uses a non-flexible rod form carrier 26 within the tip form vessel 12 instead of the thread form carrier 17. In regard to the thread form carrier 26, the top side thereof is installed by means of a centering member 27 that engages and is installed to an approximately funnel form transitive section from the wide tube 13 of the tip form vessel 12 to the narrow tube 15, and the bottom side thereof is installed by means of an installed centering member 28, that engages and is installed to the opening 16 of the tip form vessel 12.

As shown in FIG. 1(*e*), the centering member 27 is provided to a tapered engaging tube 31, and it has a plurality of supporting plates 31*a* that are formed in a radial form from an axle 30, to which the rod form carrier 26 is installed, that is formed along the central axis of the engaging tube 31. Furthermore, as shown in FIG. 1(*f*), the centering member 28 is provided to a cyclically formed flange 34, and it has a plurality of supporting plates 33*a* that are formed in a radial form from an axle 32, to which the rod form carrier 26 is installed, that extend along the aforementioned central axis. Consequently, although the passage of fluid is possible through the centering members 27 and 28, it corresponds to a carrier passage blocking member of the enclosing section that encloses the rod form carrier 26 in the narrow tube 15, such that the rod form carrier 26 is not discharged from the opening 16.

Figure 1:
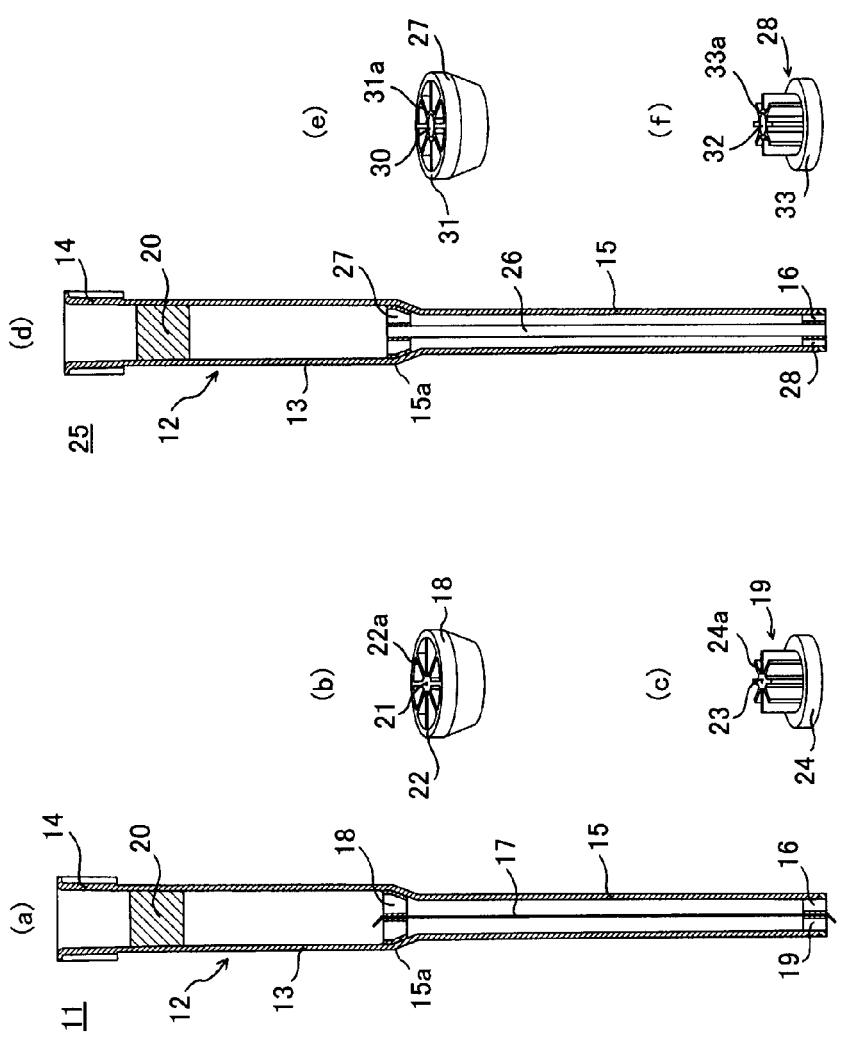
FIG. 1 is a drawing showing a biological material fixed carrier enclosing tip according to a first and a second embodiment.
Figure 2:
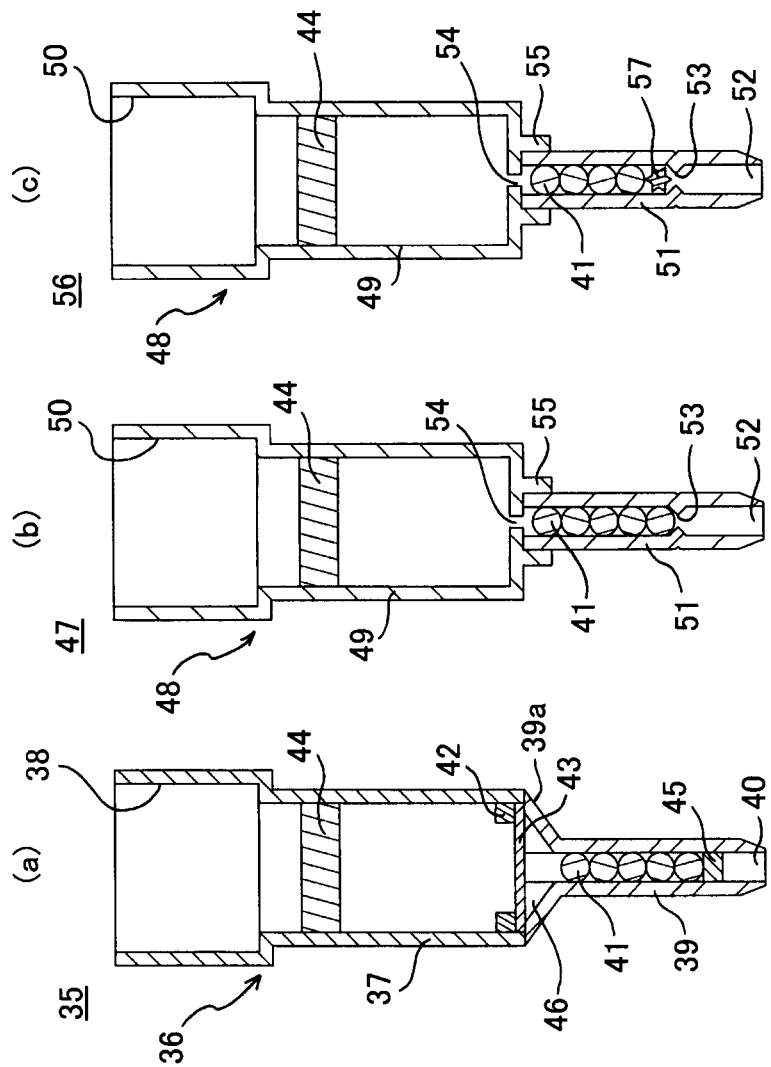
FIG. 2 is a cross-sectional view showing a biological material fixed carrier enclosing tip according to a third to a fifth embodiment.

FIG. 2(a) shows a cross-sectional schematic view of a biological material fixed carrier enclosing tip 35 according to a third embodiment of the present invention. The biological material fixed carrier enclosing tip 35 has a tip form vessel 36, which has a translucency, that has a wide tube 37 as the storage section, and a narrow tube 39 that is formed narrower than the wide tube 37. The upper end of the wide tube has an installation opening part 38 that is to be installed to a nozzle, which is not shown in the drawing, that performs suction and discharge of gas. An opening 40, through which fluid inflow and outflow is possible by means of the suction and discharge of gas, is provided on the end of the narrow tube 39.

A filter 44 is installed on the somewhat lower side of the installation opening part 38 of the wide tube 37, and it is possible for gas to pass therethrough. Furthermore, on the bottom side of the wide tube 37, a thin mesh form member 43, which is the carrier passage blocking section, is provided by utilizing an approximately funnel form transitive section 39a between the narrow tube 39 and the wide tube 37, and it is held by a ring 42. In regard to the transitive section 39a, a plurality of supporting plates 46 that are supported by the transitive section 39a, are provided in order to support the mesh form member 43. A plurality of particle form carriers 41 (five in this example) are stored within the narrow tube 39, and on the lower side thereof, a pierced porous member 45, in which passage of fluid is possible, is installed to the narrow tube 39 as the carrier passage blocking member. It is preferable to install the porous member 45 such that a restriction or step difference formed on the narrow tube 39 is utilized.

Here, the outer diameter of the particle form carrier 41 is, for example, approximately 1.8 mm, the inner diameter of the narrow tube is, for example, approximately 2.0 mm, and the length between the pierced porous member 45 and the mesh form member 43 is, for example, approximately 50 mm.

Furthermore, in a case where a plurality of particle form carriers are arranged, in order to make the arrangement position clear, it is preferable to apply coloration, or to arrange standard particle carriers that have been coated by a fluorescent material in a predetermined position.

FIG. 2(b) shows a cross-sectional view of a biological material fixed carrier enclosing tip 47 according to a fourth embodiment of the present invention. The biological material fixed carrier enclosing tip 47 has a tip form vessel 48, which has a translucency, that has a wide tube 49 as the storage section, and a narrow tube 51 that is formed thinner than the wide tube 49 and is detachably provided with respect to the wide tube 49. The upper end of the wide tube 49 has an installation opening part 50 that is to be installed to a nozzle, which is not shown in the drawing, that performs suction and discharge of gas. An opening 52, through which fluid inflow and outflow is possible by means of the suction and discharge of gas, is provided on the end of the narrow tube 51. In regard to the lower end of the wide tube 49, the narrow tube 51 is, with respect to an engaging section 55 that is provided such that it surrounds a hole 54 that is provided such that it passes through the central axis thereof, engageably provided to the upper side thereof. In a case where the upper end of the narrow tube 51 has engaged the engaging section 55, it is preferable to perform welding by means of ultrasonic waves, an adhesive, or heat, such that the narrow tube 51 does not detach. The tip form vessel 48 is, for example, formed by glass, polyethylene, polystyrene, or polypropylene.

Furthermore, a plurality of particle form carriers 41 (five in this example) are stored within the narrow tube 51. On the lower side of the narrow tube 51 thereof, a small hole or a space of a level in which the passage of the particle form carriers 41 is blocked, and a protrusion section 53 that protrudes in the radial direction thereof such that a hole is formed in which the passage of fluid is not obstructed by the presence of the particle form carriers, are provided. The size of the hole provided on the lower end of the wide tube 49 is a size in which the passage of the particle form carriers 41 is blocked. The particle form carriers 41 are formed by a water absorbing material, a porous plastic, a resin, or the like.

Here, for example, the outer diameter of the narrow tube is approximately 2.5 mm, and the inner diameter is approximately 2 mm. Furthermore, the outer diameter of the engaging section 55 is approximately 5 mm, and the inner diameter thereof corresponds to the outer diameter of the narrow tube. Furthermore, the length from the protrusion section 53 to the hole 54 is, for example, approximately 50 mm, and the diameter of the hole 54 is, for example, approximately 1 mm such that the particle form carriers 41 do not pass through, and the length of the wide tube 49 is, for example, 50 mm.

FIG. 2(c) shows a cross-sectional view of a biological material fixed carrier enclosing tip 56 according to a fifth embodiment of the present invention. The biological material fixed carrier enclosing tip 56 differs to the biological material fixed carrier enclosing tip 47 according to the fourth embodiment shown in FIG. 2(b) in that a particle form carrier 57 with concavities and convexities on the surface is substituted as a replacement for the particle form carrier 41 that is arranged at the lower end of the particle form carriers 41 that are enclosed within the narrow tube 51. Consequently, a situation in which the particle form carrier 41 adheres to the protrusion section 53 and obstructs the flow of fluid can be prevented.

Figure 3:
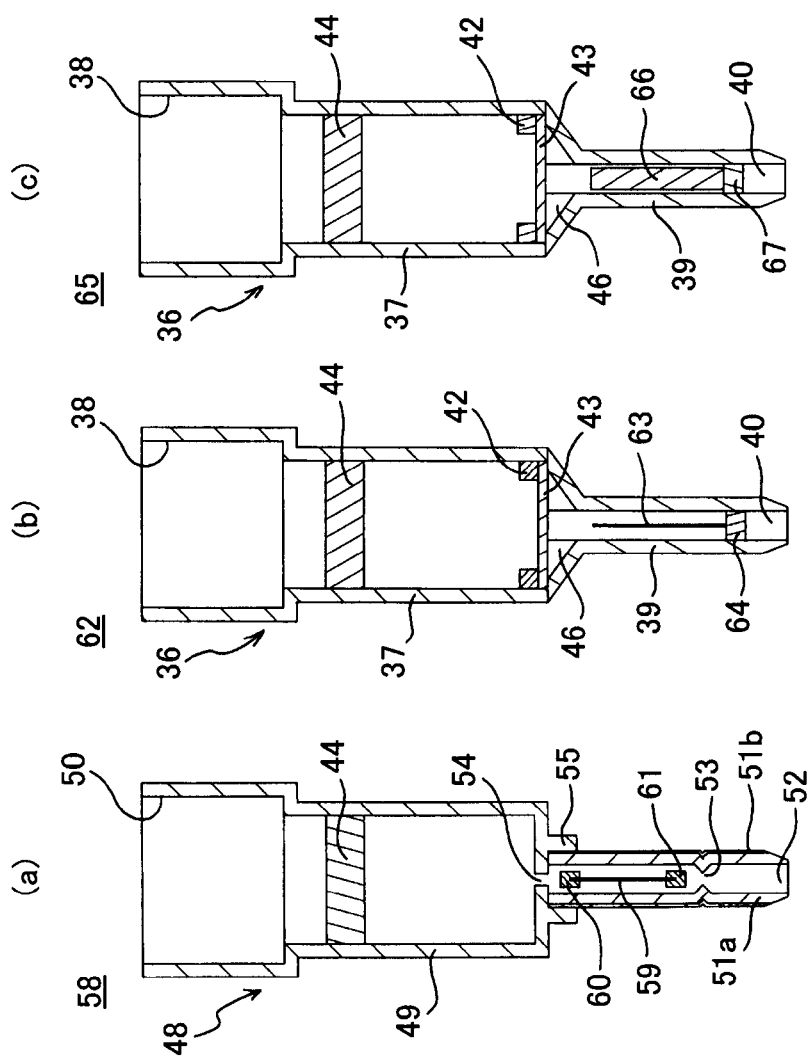
FIG. 3 is a cross-sectional view showing a biological material fixed carrier enclosing tip according to a sixth to an eighth embodiment.

FIG. 3(a) shows a cross-sectional view of a biological material fixed carrier enclosing tip 58 according to a sixth embodiment of the present invention. The biological material fixed carrier enclosing tip 58 differs from the biological material fixed carrier enclosing tips 47 and 56 of the fourth and the fifth embodiments described in FIG. 2(b) and FIG. 2(c) in that a non-flexible wire form carrier 59 is enclosed within the narrow tube 51 instead of the particle form carrier 41. The wire form carrier 59 is installed at the upper end and the lower end thereof to installation members 60 and 61 that are formed wider than the wire of the wire form carrier 59. By forming the size of the installation sections 60 and 61 larger than the inner diameter of the hole 54 and the protrusion section 53, discharge from the installation members 60 and 61, and accordingly, the wire form carrier 59 from the opening 52, is obstructed. The installation members 60 and 61 themselves are not installed to the narrow tube 51, and therefore, they are not fixed with respect to the tip form vessel 48. For example, a portion of the wall of the narrow tube 51, that is to say, the outside portion, is formed with a conductive thin film 51b with a predetermined resistance value, and it is heatable to a predetermined temperature by flowing an electrical current to the conductive thin film 51b.

FIG. 3(b) shows a cross-sectional schematic view of a biological material fixed carrier enclosing tip 62 according to a seventh embodiment of the present invention. The biological material fixed carrier enclosing tip 62 differs to the biological material fixed carrier enclosing tip 35 according to the first embodiment in that a non-flexible wire form carrier 63 is enclosed within the narrow tube 39 instead of a plurality of particle form carriers 41. However, it differs from the biological material fixed carrier enclosing tip 58 according to the sixth embodiment in that the non-flexible wire form carrier is installed within the narrow tube 39 by means of an installation member 64 that passes fluid, and it is fixed with respect to the tip form vessel 36. The non-flexible wire form carrier 63 is installed such that it is maintained along the central axis of the narrow tube 39.

FIG. 3(c) is a cross-sectional schematic view of a biological material fixed carrier enclosing tip 65 according to an eighth embodiment of the present invention. The biological material fixed carrier enclosing tip 65 differs to the biological material fixed carrier enclosing tip 62 according to the seventh embodiment in that a non-flexible rod form carrier 66, which has a wide width, is installed and enclosed within the narrow tube 39 by means of an installation member 67 that passes fluid. The installation member 67 is, for example, a pierced porous member.

Figure 4:
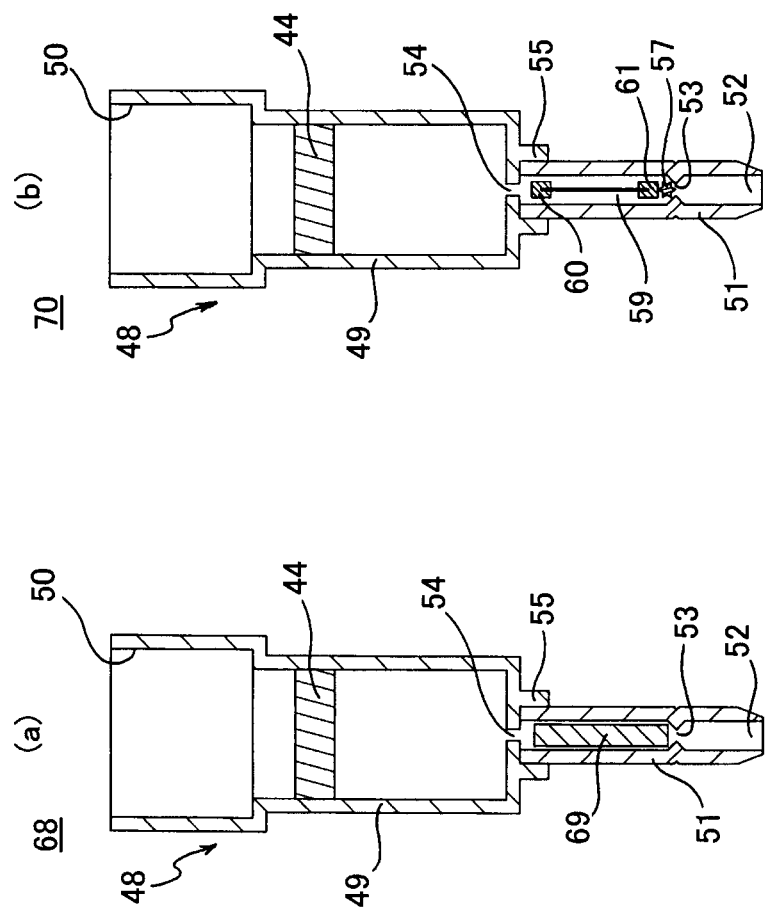
FIG. 4 is a cross-sectional view showing a biological material fixed carrier enclosing tip according to a ninth and a tenth embodiment.

FIG. 4(a) is a cross-sectional schematic view of a biological material fixed carrier enclosing tip 68 according to a ninth embodiment of the present invention. The biological material fixed carrier enclosing tip 68 differs to the biological material fixed carrier enclosing tip 65 according to the eighth embodiment in that a rod form carrier 69 is enclosed within the narrow tube 51 without being fixed. Since the thickness of the rod form carrier 69 is larger than the hole or the space formed within the narrow tube by means of the protrusion section, it is not discharged from the opening 52.

FIG. 4(b) shows a biological material fixed carrier enclosing tip 70 according to a tenth embodiment of the present invention. The biological material fixed carrier enclosing tip 70 differs to the biological material fixed carrier enclosing tip 58 according to the fourth embodiment in that it has a particle form carrier 57 that has concavities and convexities on the surface, and the installation member 61, to which the needle form carrier 59 is installed, is prevented from sealing of the hole formed by the protrusion section 53.

Figure 5:
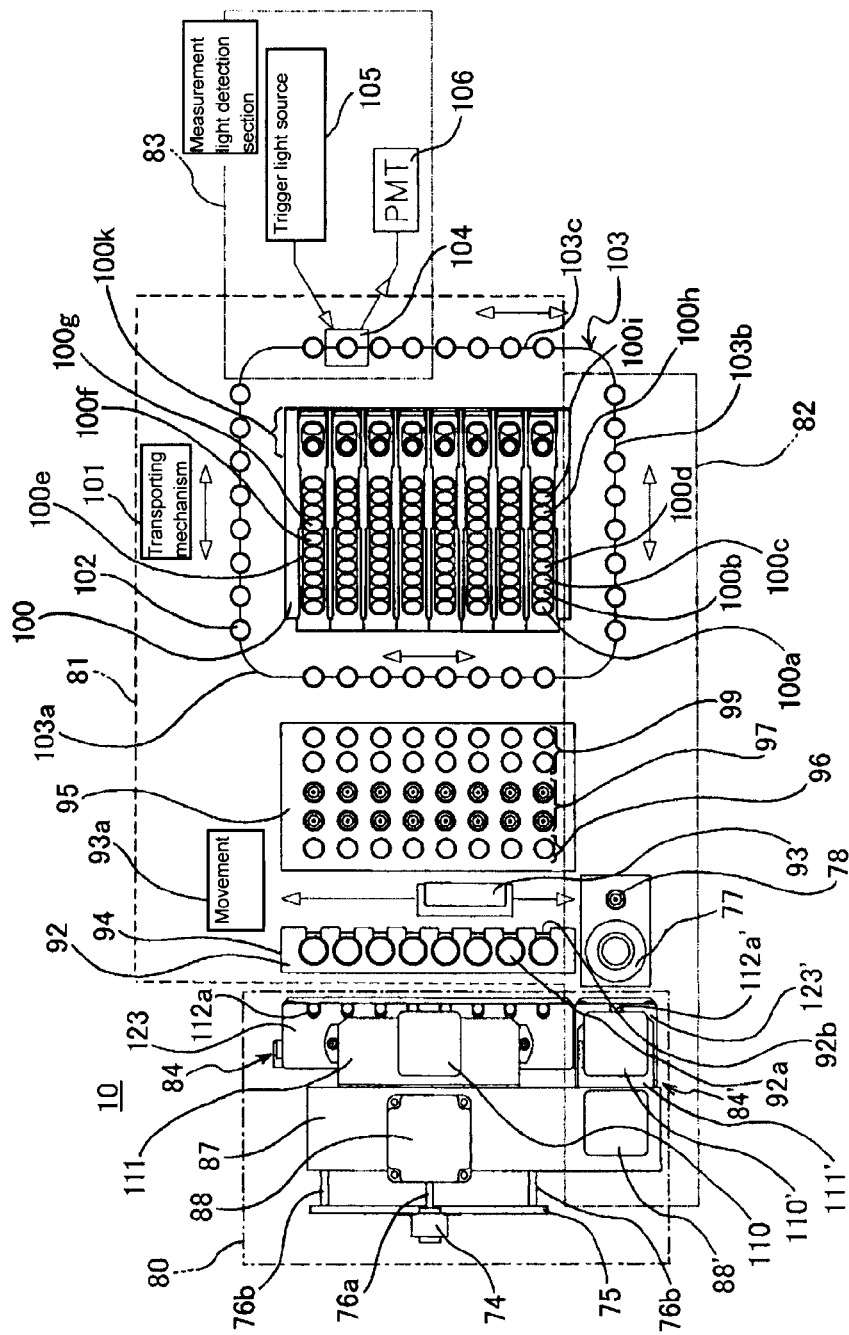
FIG. 5 is a plan view showing an entire biological material fixed carrier treatment apparatus according to an eleventh embodiment.

FIG. 5 is a planar schematic view representing an entire biological material fixed carrier treatment apparatus 10 according to an eleventh embodiment of the present invention.

The biological material fixed carrier treatment apparatus 10 has: a biological material fixed carrier enclosing tip processing device 80, which has a suction and discharge mechanism, and installs the biological material fixed carrier enclosing tip 35 on a nozzle, and performs a suction and discharge process with respect to the biological material fixed carrier enclosing tip 35; a tip processing region 81 for performing, suction and discharge with respect to the biological material fixed carrier, dispensing into an exterior vessel, stirring, washing, extraction, transport, reaction, or the like, by performing suction or discharge of a suspension containing various specimens, reagents, or the like, within the biological material fixed carrier enclosing tip 35; a reagent dispensing region 82 for dispensing a reagent for measurement, or the like, to within the biological material fixed carrier enclosing tip by using a single nozzle possessed by the biological material fixed carrier enclosing tip processing device 80; and a measurement region 83 that obtains optical information for executing measurement in regard to the biological material fixed carrier that is enclosed within the biological material fixed carrier enclosing tip 35.

Figure 6:
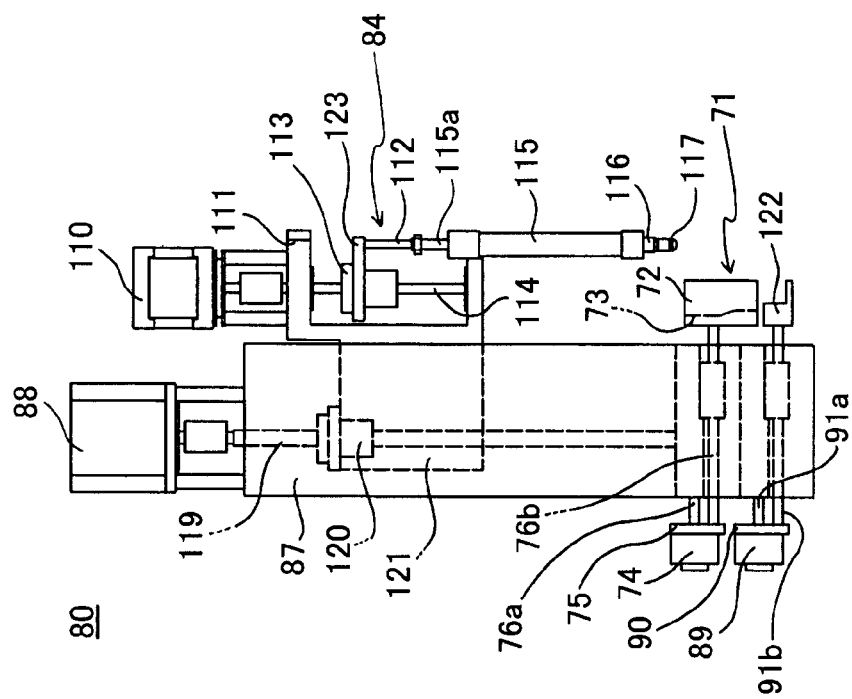
FIG. 6 is a side view showing a side view of a biological material fixed carrier enclosing tip treatment apparatus according to a twelfth embodiment.

In regard to the biological material fixed carrier enclosing tip processing device 80 shown in FIG. 5 and FIG. 6, suction and discharge of gas is performed using a nozzle that is communicated with a collective suction and discharge mechanism and an individual suction and discharge mechanism. The biological material fixed carrier enclosing tip processing device 80 has a collective nozzle head 84 that has a plurality (eight consecutive in this example) of nozzles 117 that are arranged in the column direction (the vertical direction in the drawing), and an individual nozzle head 84' that has a single nozzle that performs suction and discharge independently to the collective nozzle head 84. In regard to the collective nozzle head 84, as opposed to the suction and discharge being simultaneously performed by the collective suction and discharge mechanism with respect to the plurality of consecutive nozzles 117, the suction and discharge is performed with respect to the nozzle of the individual nozzle head 84' independently to the eight consecutive nozzles 117 by an individual suction and discharge mechanism. In the drawing, the reference symbols of the components, or the like, that belong to the individual nozzle head 84' are indicated by attaching a dash to the reference symbol of the components, or the like, that belong to the corresponding collective nozzle head 84.

In FIG. 6, only the collective suction and discharge mechanism of the collective nozzle head 84 is shown. As shown in FIG. 6, the collective suction and discharge mechanism has an engaging section 116 that is provided to a somewhat upper section than the lower end of the nozzle 117, and a rod 112 for sliding a plunger 115a within a cylinder 115 that is joined to the nozzle 117. Furthermore, the eight rods 112 are installed in eight respective notch sections that are provided on the edge of a driving plate 123 (reference symbol 123' represents a driving plate of the individual suction and discharge mechanism) in which vertical movement is possible for each, such that they sit on eight consecutive end sections 112a (reference symbol 112a' represents an end portion of the individual suction and discharge mechanism), that have a larger diameter than the diameter of the rods 112 and protrude in the radial direction. Hence, the collective nozzle head 84 and the individual nozzle head 84' simultaneously move in the row direction (the horizontal direction or the left and right directions on the drawing).

Furthermore, as shown in FIG. 6, the driving plate 123 is joined to a nut section 113 that screws to a ball screw 114. The rods 112 are energized in the downward direction at all times by means of a spring that is provided to the cylinder 115. Consequently, the rods 112 are able to be raised by the nut sections 113 in a case where they move in the upward direction, but in a case where they are lowered in the downward direction, they are lowered not as a result of the nut sections 113, but because of the spring force. The ball screws 114 are rotationally driven by a motor 110 (reference symbol 110' represents the motor of the individual suction and discharge mechanism) provided to a cross-sectional U-shaped supporting member 111 (reference symbol 111' represents the supporting member of the individual suction and discharge mechanism), and as a result, the driving plate 123 and the eight rods 112 vertically move.

In regard to the raising and lowering of the nozzle itself, although it is independent of the individual nozzle head 84' and the collective nozzle head 84, the horizontal movement in the row direction (the left and right directions in FIG. 7) is integrated. The individual nozzle head 84' is, in regard to the reagent dispensing region 82, used for dispensing reagents for measurement within the biological material fixed carrier enclosing tip 35, or the like, that are stored within the tip storage section 102. In the reagent dispensing region 82, a reagent storage section 77 that stores predetermined reagents that are suctioned by the nozzle head 84', and a predetermined tip 78, which is in a state where it is installable to the nozzle head 84', for example, a filter-containing tip, are provided. Furthermore, the reagent storage section 77 is, for example, provided with a constant temperature device for retaining the reagents at a constant temperature.

In FIG. 6, the inside of the chassis 87, has a ball screw 119, a nut section 120 that screws to the ball screw 119, and a supporting body 121 that has the supporting member 111, to which the nut section 120 is installed, at one end. Furthermore, on the chassis 87, a motor 88 that rotationally drives the ball screw 119 is provided. By means of a vertical movement mechanism resulting from these components, the nozzle 117 is vertically movable.

A temperature raising and lowering device 71 is provided on the lower side of the chassis 87. In regard to the temperature raising and lowering device 71, it is formed along the column direction such that it has a height and a width that primarily makes it approachable to, or able to make contact with, the narrow tube of the eight tips that are installed to the eight consecutive nozzles, it has a heating plate 73 that has a heater in the interior, and nine heating walls 72, which are installed to the heating plate 73, that have a heater in the interior and are provided protruding such that they respectively sandwich the tips from both sides, and this heating plate 72 and these nine heating walls 72 are, as a whole, formed in a comb form. Furthermore, it is preferable for the heating plate 73 to be formed such that it has a shape that is matched to the shape of the tip that becomes the subject of temperature control. Here, the heating plate 73 and the heating walls 72 correspond to the temperature raising and lowering body.

The temperature raising and lowering body 71 approaches, or makes contact with, the tip installed to the nozzle 117 of the collective nozzle head 84, and it has a motor 74 for making it possible to heat the tip, a ball screw 76a that is rotationally driven by the motor 74, a nut section 75 that screws onto the ball screw 76a, and a movement rod 76b that joins the nut section 75 and is movable in the left and right directions in the drawing, and also joins to the heating walls 72 and the heating plate 73.

The bottom side of the temperature raising and lowering device 71 has a motor 89 for making it possible to remove the tip that has been installed to the nozzle 117 of the collective nozzle head 84, a ball screw 91a that is rotationally driven by the motor 89, a nut section 90 that screws onto the ball screw 91a, and a movement rod 91b that joins the nut section 90 and is movable in the left and right directions in the drawing, and which moves a claw 122 in the left and right directions in the drawing.

The biological material fixed carrier enclosing tip processing device 80 is provided such that it is suspended from the upper side, and it is movably provided by means of an X axis (row direction) movement mechanism not shown in the drawing, which utilizes a direct acting mechanism, such that it covers all regions of the biological material fixed carrier treatment apparatus 10 and the other necessary regions.

Furthermore, returning to FIG. 5, the tip processing region 81 has: a cartridge vessel 92, which has eight consecutive specimen wells 92a that store the suspension in which the specimen is suspended; a matrix form vessel 95, which, as well as storing various tip type columns 96 and 97, has a 5 column 8 row well having a liquid storage section column 99 that stores the product material; and eight cartridge vessels 100 that have a prepackable well 100a for storing various reagents or materials that are necessary for executing processing, or storing the resulting material of processing. Amongst the cartridge vessels 101, reference symbol 100b represents an incubator well that is provided with a heat block.

Furthermore, barcodes 92b are attached to the specimen storage wells 92a, that display information relating to the respective specimens thereof. The barcodes 92b are read by a barcode reading section 93, which reads the barcode 92b, by moving such that it scans. Reference symbol 93a is a movement mechanism that drives the barcode reading section 93.

A movable conveyor 103, which is made to surround the surroundings of the eight consecutive cartridge vessels 100, is provided along a square shaped transporting route that has the column transporting routes 103a and 103c on the movement route of the collective nozzle head 84 of the biological material fixed carrier enclosing tip processing device 80 along the column direction (the vertical direction or the Y direction in the drawing), which is parallel to the arrangement direction of the eight consecutive nozzles, and a row transporting route 103b on the movement route of the individual nozzle head 84' along the row direction (the horizontal direction or the X direction), which is perpendicular to the arrangement direction.

The conveyor 103 corresponds to the queued route transporting device, and in regard to the conveyor 103, a total of 32 tip storage sections or tubes 102, which correspond to the transport storage section, are movably joined together with the conveyor 103, such that they correspond to the spacing between the nozzles. Consequently, in regard to a position such as the one shown in FIG. 5, suction and discharge of liquid with respect to the two columns of tip storage section 102 groups arranged on the column transporting routes 103a and 103c are possible by means of the eight consecutive nozzles of the biological material fixed carrier enclosing tip processing device 80. Furthermore, by means of the series of nozzles of the individual nozzle head 84', which is provided such that suction and discharge is possible independently to the group of eight consecutive nozzles of the collective nozzle head 84 of the biological material fixed carrier enclosing tip processing device 80, within the transporting route, which has been arranged in a square shape as the queued route transporting device, the row transporting route 103b of the lower side, that is to say, with respect to the selected tip storage sections 102 within the reagent dispensing region 82, reagents that correspond to an object, for example, a substrate liquid, or the like, in chemiluminescence, can be dispensed. In particular, it is dispensed directly before reaction of the PCR reaction liquid, or the like, in PCR preprocessing for a case where DNA extraction is performed.

Furthermore, within the measurement region 83, a measurement position 104 is provided within the square shaped transporting route of the queued route transporting device, and in regard to the measurement position 104, excitation light is irradiated within the biological material fixed carrier enclosing tip by means of the trigger light source 105, and measurement is performed by receiving the generated light at the light receiving section 106. Consequently, processing can be performed according to the processing object for each tip.

Figure 7:
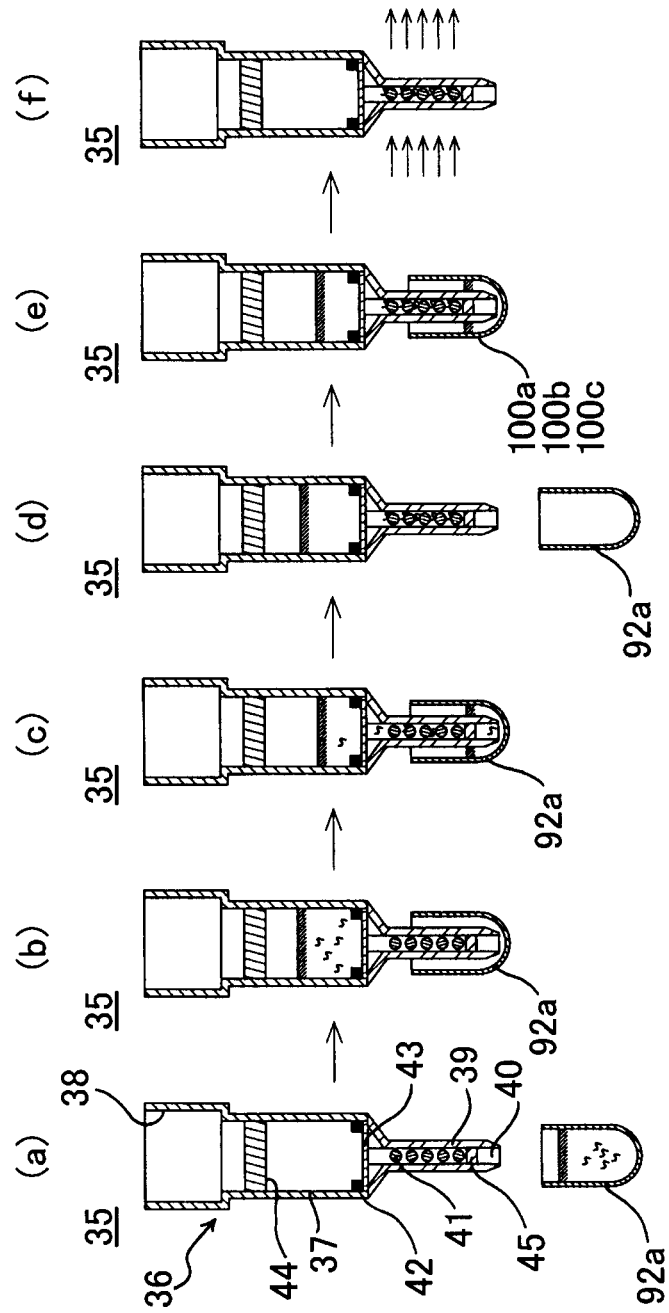
FIG. 7 is a flow diagram showing a biological material fixed carrier treatment method according to a thirteenth embodiment.

Next, based on FIG. 7, as DNA processing according to the present embodiment, SNPs (single nucleotide polymorphism) typing is explained for a case where the biological material fixed carrier enclosing tip 35 is used.

At the plurality of SNP positions that are to be measured, an oligonucleotide, which has a possibility of hybridization, that has a base sequence, is fixed to the particle form carrier 41 as a probe material. In order to perform fixing to the particle form carrier 41, a functional group is generated or expressed beforehand at the surface of the particle form carrier 41, it is bonded with the probe material, and the surface is cleaned with a suitable solvent.

For example, at SNP1 (a first position), there is a possibility of two types, the base T or the base C, and at SNP2 (a second position), there is a possibility of two types, the base G or the base A.

A particle form carrier 41 fixed with a base sequence for determining the base T at SNP1, a particle form carrier 41 fixed with a base sequence for determining the base C at SNP1, a particle form carrier 41 fixed with a base sequence for determining the base G at SNP2, and a particle form carrier 41 fixed with a base sequence for determining the base A at SNP2 are, as shown in FIG. 7(a), provided with a pierced porous member 45 within the narrow tube 39 of the tip form vessel 36, which has a translucency, and the particle form carriers 41 are placed in the aforementioned order (five carriers in this example), and by performing enclosing by providing a mesh form member 43, the biological material fixed carrier enclosing tip 35 is formed.

For example, in regard to eight test subjects, a case where the SNPs typing position of a respective plurality of positions (two positions in this example) are attempted to be simultaneously determined, is explained. In this case, in a step S1, in regard to a biological material fixed carrier enclosing tip 35 that is formed in this manner, the nozzle 117 of the biological material fixed carrier enclosing tip processing device 80 is installed to the installation opening part 38 provided on the upper end of the wide tube 37 thereof.

On the other hand, specimens such as the following are stored in the eight specimen storage wells 92a provided in the tip processing region 81. That is to say, the genome is respectively extracted from the blood of the eight test subjects, and amongst these genomes, the fragments that contain a plurality of positions of the SNPs typing positions are amplified by a thermal cycler, a material that is labeled by a fluorescent material is generated, and this is stored per test subject in the eight specimen wells 92a. Furthermore, in the eight consecutive cartridge vessels 100, a BW buffer solution is stored in the wells 100a to 100c thereof.

In a step S2, as shown in FIG. 7(b), the collective nozzle head 84 of the biological material fixed carrier enclosing tip processing device 80 is advanced in the row direction by means of the movement device, the narrow tubes 39 are simultaneously inserted into the specimen storage wells 92a, and the inside of the narrow tubes 39 are simultaneously filled by performing suction of a suspension that is inside the specimen storage wells 92a.

In a step S3, as shown in FIG. 7(c), the plurality of particle form carriers 41 and the suspension are brought into sufficient contact via the nozzle, for example, by stirring as a result of repeating suction and discharge ten times at a predetermined speed s1 (for example, approximately 200 microliters/sec), and in an amount v1 (for example, approximately 400 microliters).

Then, in a step S4, as shown in FIG. 7(d), the DNA fragments within the suspension, which have been labeled by a fluorescent material, bond to the corresponding particle form carrier 41 amongst the positions of the SNP by means of hybridization. The residual liquid is discharged into the specimen storage well 92a.

In a step S5, in regard to the biological material fixed carrier enclosing tip processing device 80, the biological material fixed carrier enclosing tip 35 that encloses the particle form carrier, for which the reaction has been completed, is transported to the location of the wells 100a of the eight consecutive cartridge vessels 100, and with respect to the BW buffer solution, cleaning is performed by repeating suction and discharge ten times, for example, by means of a predetermined speed s2 (for example, from approximately 760 to 1700 microliters/sec) in a microamount v2 (for example, approximately 500 microliters). Furthermore, the same operation is repeated with respect to the wells 100b and 100c.

In a step S6, in regard to the biological material fixed carrier enclosing tip 35, for which cleaning has been completed, the collective nozzle head 84 is moved to the position of the tip storage section 102 that is stopped on the column transporting route 103a of the conveyor 103, separated from the plurality of consecutive nozzles 117 provided to the collective nozzle head 84a by means of the claw 122 and stored in the tip storing section 102, and transported along the transporting route by driving the conveyor 103. At the time the tip storage section 102 reaches the row transporting route 103b, following suction of a predetermined reagent by moving the individual nozzle head 84' to the reagent storage section 77, amongst the eight tip storage sections 102 that are stopped along the row transporting route 103b, dispensing of a reagent for measurement is performed from the installation opening part 38 of the selected biological material fixed carrier enclosing tip 35, for example, as the predetermined reagent. Thereafter, it is transported to the measurement position 104 provided on the transporting route by driving the conveyor 103, an excitation light is irradiated at the measurement position, and the light within the narrow tube 39 is received at the light receiving section 106. By performing measurement of the light emission position, analysis of the structure of the target material is performed.

Figure 8:
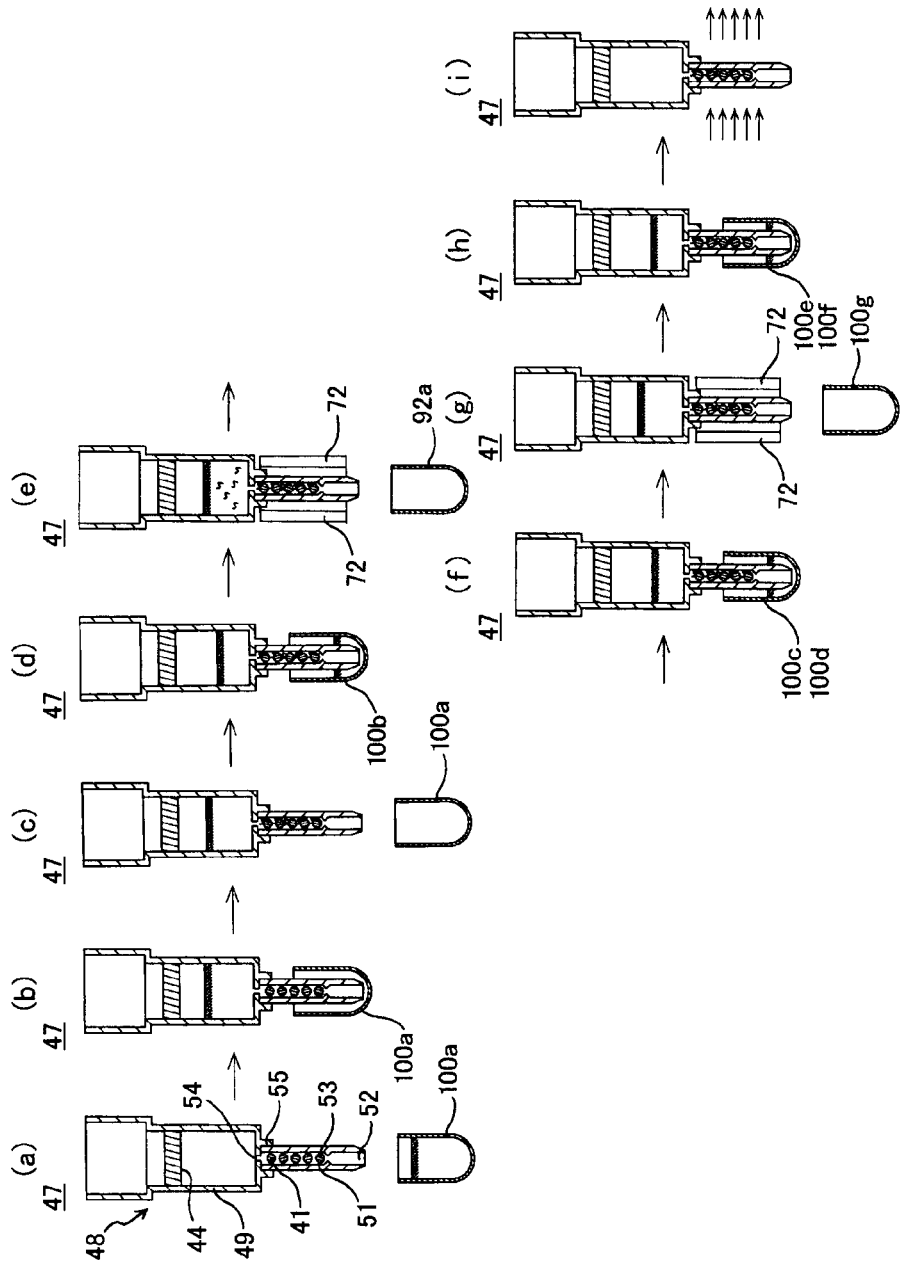
FIG. 8 is a flow diagram showing a biological material fixed carrier treatment method according to a fourteenth embodiment.

Next, based on FIG. 8, the processing procedure with respect to an allergy test as a protein analysis example is shown for a case where the biological material fixed carrier enclosing tip 47 is used.

Various allergen materials, for example, materials obtained from cedar pollen, ragweed, mites, mold, or the like, are fixed to the particle form carriers 41. In order to fix the allergen materials to the particle form carriers 41, a functional group is generated or expressed beforehand on the surface of the particle form carriers 41. In regard to these allergen materials, as shown in FIG. 8(a), the fixed particle form carriers 41 are placed in this order within the narrow tube 51 (five in this example), which has a translucency, the narrow tube 51 engages the engaging section 55 of the wide tube 49, is installed by welding as a result of adhesion, ultrasonic waves or heat, and is enclosed, and the biological material fixed carrier enclosing tip 47 is formed.

In a step S11, in regard to the biological material fixed carrier enclosing tip 47 obtained in this manner, the nozzle 117 of the biological material fixed carrier enclosing tip processing device 80 is installed to the installation opening part 50 provided to the upper end of the wide tube 49 thereof.

On the other hand, blood collected from the eight test subjects is stored in the specimen storage wells 92a provided to the tip processing region 81, and in the eight consecutive cartridge vessels 100, a 50 mM TBS buffer solution and a pH 8, 1% BSA solution are stored in the wells 100a, a cleaning solution comprising a 50 mM TBS buffer solution and a pH 8, 0.005% Tween solution are stored in the wells 100b to 100f, and a liquid that suspends an anti-human IgE antibody that has been labeled with a fluorescent material is stored in the wells 100g.

In a step S12, as shown in FIGS. 8(a), (b) and (c), the solutions are stirred by performing suction and discharge of an amount v3 (for example, approximately 500 microliters) of the solution stored in the wells 100a at a speed s3 (for example, approximately 760 microliters/sec), and blocking (shutoff) of the particle carrier 41 surfaces is performed.

In a step S13, as shown in FIG. 8(d), cleaning is performed with the 50 mM TBS buffer solution and pH 8, 0.005% Tween solution that is stored in the wells 100b. Furthermore, in a step S14, as shown in FIG. 8(e), the biological material fixed carrier enclosing tip 47 installed to the nozzle is moved to the specimen storage well 92a, the blood stored in the specimen storage well 92a is suctioned into the narrow tube 51 and brought into contact, and the IgE antibody in the blood and the allergen material is reacted within the narrow tube 51 for 30 minutes at 37 degrees. At that time, in order to maintain the narrow tube 51 at a constant temperature, it is heated such that the narrow tube 51 is sandwiched from both sides and two plates amongst the heating plates 72 of the temperature raising and lowering device 71, which are arranged in a comb form, approach both sides of the eight consecutive biological material fixed carrier enclosing tip 47. Consequently, the inside of the narrow tube 51 is efficiently heated with certainty.

Next, in a step S15, as shown in FIG. 8(f), the biological material fixed carrier enclosing tip 47 is moved to the wells 100c of the cartridge vessel 100. The aforementioned cleaning solution is stored in the wells 100c, and cleaning is performed by repeating suction and discharge ten times at, for example a speed s4 (for example, from approximately 760 microliters to 1700 microliters/sec) and in an amount v4 (for example, approximately 500 microliters). Furthermore, the biological material fixed carrier enclosing tip 47 is transported to the wells 100d, and cleaning is repeated.

Next, in a step S16, as shown in FIG. 8(g), the collective nozzle head 84 is moved to the wells 100g, the suspension is suctioned and brought into contact with the particle form carrier 41 in order to react with the anti-human IgE antibody stored in the wells 100g, which has been labeled with fluorescent light, and it is maintained at 37° C. for 30 minutes. Also in this case, as mentioned above, the inside of the narrow tube is heated by approaching the heating plates 72 of the temperature raising and lowering device 71 such that they sandwich both sides of the biological material fixed carrier enclosing tip 47.

In a step S17, as shown in FIG. 8(h), it is moved to the wells 100e of the cartridge vessel 100, and the particle form carrier 41 is cleaned by performing suction and discharge of the stored cleaning solution approximately ten times, for example, at a speed s5 (for example, from approximately 760 microliters to 1700 microliters/sec), and in an amount v5 (for example, 500 microliters). The same operation is repeated following movement to the wells 100f.

Next, in a step S18, in regard to the biological material fixed carrier enclosing tip 47, the collective nozzle head 84 is moved to the tip storage section 102 that is stopped on the column transporting route 103a of the conveyor 103, separated from the plurality of consecutive nozzles 117 provided to the collective nozzle head 84 by means of the claw 122 and stored in the tip storing section 102 that is arranged on the column transporting route 103a, and transported along the transporting route by driving the conveyor 103. At the time the tip storage section 102 reaches the position of the row transporting route 103b, the individual nozzle head 84' is moved to the reagent storage section 77, which stores the predetermined test reagent, the reagent is suctioned, and amongst the eight tip storage sections 102 that are stopped along the row transporting route 103b, it is moved to the selected biological material fixed carrier enclosing tip 47, and dispensing of the predetermined reagent is performed from the installation opening part 50 of the selected biological material fixed carrier enclosing tip 47. Thereafter, at the measurement position 104 provided on the transporting route, light from the carrier is received and measured at the light receiving section 106, the fluorescence strength of the particle surface is measured, and the reacted allergen material is specified.

Figure 9:
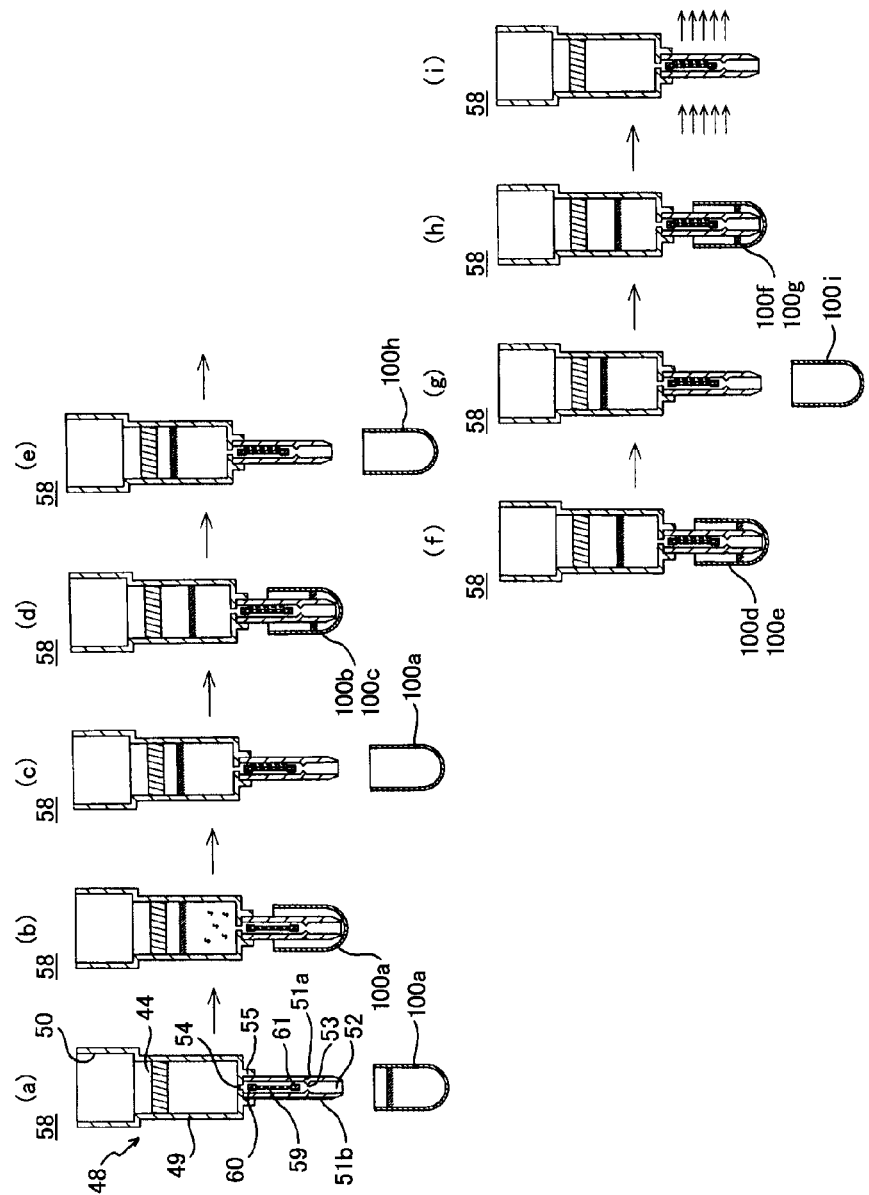
FIG. 9 is a flow diagram showing a biological material fixed carrier treatment method according to a fifteenth embodiment.

Next, based on FIG. 9, a protein analysis example using a non-flexible needle form carrier, to which the protein is fixed, is explained for a case where the biological material fixed carrier enclosing tip 58 is used. In the process, in FIG. 9(a), several types (five types in this example) of protein expression base sequences and an oligonucleotide having a protein collection material that collects the expressed proteins are fixed beforehand to the non-flexible needle form carrier 59 shown in FIG. 3(a) with a spacing. In order to fix these materials, a functional group is generated or expressed on the surface of the needle form carrier 59. Consequently, the generated amount of the generated protein, and the bondability with a specific protein are examined. In the present example, the needle form carrier 59 is stored within the narrow tube 51, and it is enclosed as a result of engaging the narrow tube 51, in which the needle form carrier 59 is stored, with the engaging section 55 provided on the lower end of the wide tube 49, and installation by means of adhesion or welding, and the biological material fixed carrier enclosing tip 58 is formed.

On the other hand, within the respective single liquid storage sections 100a of the eight consecutive cartridge vessels 100 provided to the tip processing region 81 of FIG. 5, solutions of amino acids, ribosomes, or the like, are stored, a cleaning solution (hereunder referred to as "PBS-T") comprising a PBS buffer solution and a 0.05% Tween 20 buffer solution, which is a surface active agent is stored in the liquid storage sections 100b to 100g, a 5% skim milk suspension in PBS-T is stored in the liquid storage sections 100h, and a solution of an antibody labeled with a fluorescent material, and a biotinylated material is stored in the liquid storage sections 100i.

In a step S21, in regard to a biological material fixed carrier enclosing tip 58 that is formed in this manner, the nozzle 117 of the biological material fixed carrier enclosing tip processing device 80 is installed to the installation opening part 50 provided on the upper end of the wide tube 49 thereof. Next, as shown in FIGS. 9(a), (b) and (c), the eight consecutive nozzles 117 of the collective nozzle head 84 of the biological material fixed carrier enclosing tip processing device 80 are simultaneously moved to the liquid storage section 100a of the cartridge vessels 100, and an amount v6 (for example, approximately 500 microliters) of the solution of the amino acid, or the like, that is stored in the liquid storage sections 100a is suctioned into the narrow tube 51 at a speed s6 (for example, approximately 200 microliters/sec). In this state, the inside of the narrow tube 51 is heated by, for example, flowing an electrical current to the conductive thin film 51a that forms the wall of the narrow tube 51, and it is maintained at 37° C. for 1 hour.

In a step S22, as shown in FIG. 9(d), following discharge of the liquid from the narrow tube 51, the collective nozzle head 84 is moved to the liquid storage sections 100b, and it is washed by repeating suction and discharge of the PBS-T solution with respect to the narrow tube 51, for example, ten times, at a speed s7 (for example, from approximately 760 to 1700 microliters/sec), and in an amount v7 (for example, approximately 500 microliters). This operation is also repeated at the liquid storage sections 100c.

In a step S23, as shown in FIG. 9(e), the collective nozzle head 84 is moved to the liquid storage sections 100h, the PBS-T and 5% skim milk suspension is suctioned, then reacted in a room temperature state for approximately 1 hour, and blocking is performed.

In a step S24, as shown in FIG. 9(f), following discharge of the liquid from the narrow tube 51, the collective nozzle head 84 is moved to the liquid storage sections 100d, and it is washed by repeating suction and discharge of the PBS-T solution with respect to the narrow tube 51, for example, ten times, at a speed s8 (for example, from approximately 760 to 1700 microliters/sec), and in an amount v8 (for example, approximately 500 microliters). This operation is also repeated at the liquid storage sections 100e.

In a step S25, as shown in FIG. 9(g), the biological material fixed carrier enclosing tip 58 is transported to the liquid storage sections 100i, and the suspension which suspends an antibody that has been labeled by the fluorescent material, and a biotinylated material, is suctioned, and incubated at room temperature for approximately 30 minutes to 1 hour.

Furthermore, in a step S26, as shown in FIG. 9(h), it is transported to the liquid storage sections 100f, and it is washed by repeating suction and discharge of the PBS-T solution with respect to the narrow tube 51, for example, ten times, at a speed s3. This operation is also repeated at the liquid storage sections 100g.

In a step S27, in regard to the biological material fixed carrier enclosing tip 58, the collective nozzle head 84 is moved to the tip storage section 102 that is stopped on the column transporting route 103a of the conveyor 103, separated from the plurality of consecutive nozzles 117 provided to the collective nozzle head 84 by means of the claw 122 and stored in the tip storing section 102 that is arranged on the column transporting route 103a, and transported along the transporting route by driving the conveyor 103. At the time the tip storage section 102 reaches the row transporting route 103b, the individual nozzle head 84' is moved to the reagent storage section 77, a predetermined reagent is suctioned, and amongst the eight tip storage sections 102 that are stopped along the row transporting route 103b, it is moved to the selected biological material fixed carrier enclosing tip 58, and dispensing of the predetermined reagent is performed from the installation opening part 50 of the tip 58. Thereafter, at the measurement position 104 provided on the transporting route, light from the carrier is received and measured at the light receiving section 106, the fluorescence strength of the particle surface is measured, and the protein that has reacted with the antibody labeled with the fluorescent material, the biotinylated material, or the like, is specified, or the expression amount thereof is measured from the strength and the light emission position thereof.

Figure 10:
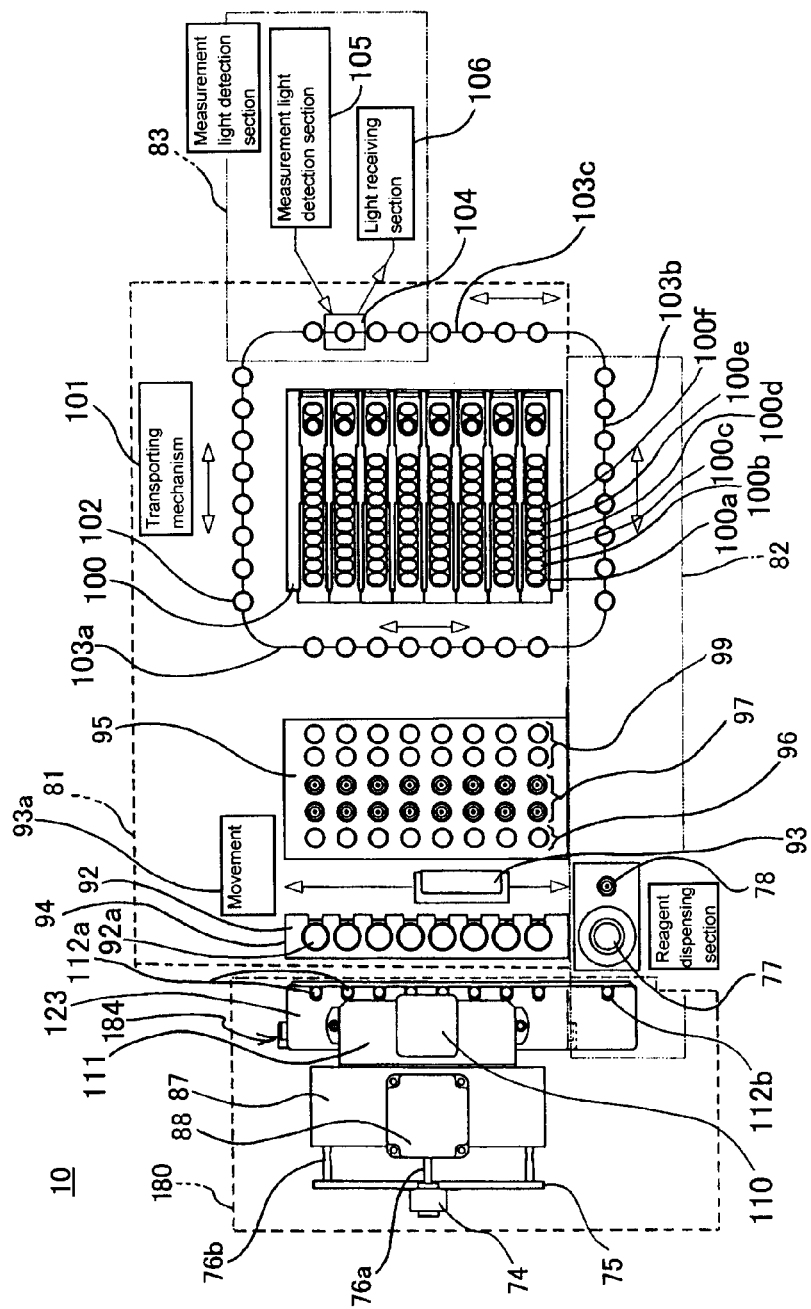
FIG. 10 is a plan view showing an entire biological material fixed carrier treatment apparatus containing another biological material fixed carrier enclosing tip treatment apparatus according to the twelfth embodiment.

Furthermore it is possible to use a biological material fixed carrier enclosing tip processing device 180 according to another embodiment shown in FIG. 10 instead of the biological material fixed carrier enclosing tip processing device 80 shown in FIG. 5 and FIG. 6. In FIG. 10, the same reference symbols as in FIG. 5 and FIG. 6 indicate the same components. The biological material fixed carrier enclosing tip processing device 180 is one in which suction and discharge of gas is performed using a nozzle that is communicated with a suction and discharge mechanism, although the biological material fixed carrier enclosing tip processing device 180 has a nozzle head 184 that has a plurality of consecutive (nine consecutive in this example) nozzles 117 that are arranged in the column direction (the vertical direction in the drawing), and with respect to the nozzle head 184, it differs to the nozzle head 84 in that suction and discharge is simultaneously performed by the same suction and discharge mechanism. Amongst the nine consecutive nozzles 117, one nozzle 117 of the end is an individual nozzle, and as shown by the position thereof (the position of reference symbol 112b in FIG. 10), it is provided such that it is somewhat separated from the eight consecutive nozzles 117, that is to say, the position of the collective nozzle (the position of reference symbol 112a in FIG. 10).

In regard to the suction and discharge mechanism, it has a wide diameter section 116 provided to a somewhat upper section of the nozzles 117, and a rod 112 for sliding a plunger 115a within a cylinder 115 that is joined to the nozzles 117. Furthermore, the nine rods 112 are installed such that they sit on eight consecutive end sections 112a and a single end section 112b, that have a larger diameter than the rods 112 and protrude in the radial direction from the eight respective notch sections that are provided to the edge of a driving plate 123, in which simultaneous vertical movement is possible. Hence, the nozzle head 184 simultaneously moves in the row direction (the horizontal direction or the left and right directions on the drawing).

Amongst the nine consecutive nozzles 117, the individual nozzle is provided to the nozzle head 184. Hence the suction and discharge is simultaneously performed together with the other eight consecutive collective nozzles. Furthermore, also in regard to the raising and lowering mechanism, it is simultaneously performed with respect to horizontal movement in the row direction (the left and right directions in FIG. 12). However, the individual nozzle is, in the reagent dispensing region 82, used for dispensing reagents for measurement into the biological material fixed carrier enclosing tip 11. In a case where the individual nozzle is used, it is in a state where the biological material fixed carrier enclosing tip has been removed from the other collective nozzles. Furthermore, in a case where the collective nozzles are used, it is in a state where the tip form vessel, or the like, is not installed to the individual nozzle.

The embodiments above have been specifically explained in order to better understand the present invention, and do not restrict other embodiments in any way. Accordingly, they are changeable within a scope that does not depart from the gist of the invention. For example, in the embodiments, although only the cases of DNA and proteins were explained, it may also be a sugar chain, other DNA materials, RNA, or the like. Furthermore, as the particle form carrier, although only the case of a spherical particle form carrier was explained, it is not restricted to this case, and it may be a cylinder shape, or a rectangular parallelopiped shape. Moreover, it can also be applied to indeterminately shaped carriers. Furthermore, in regard to the numerical values, the frequencies, the shapes, the numbers, the quantities, or the like, that were used in the explanations above, they are not restricted to these cases in any way.

Moreover, in the present invention, it may be a narrow and long member, such as a thread form, with a flexibility, or a thread form, in which one or more types of biological materials, such as a ligand, are provided such that they are fixed or are fixable to the side face thereof. In short, it can be used as the carrier as long as it is formed in a size or a shape that is passable through the opening, and suction and discharge of fluid can be performed in a state where it is maintained within the carrier storage section.

Furthermore, by suppressing the chemical material containing the ligand, or the like, with respect to all side faces of the narrow and long member to a low concentration, production is simplified and the reliability thereof is increased, and on the other hand, at the time of processing, by storing the integrated narrow and long member, the processing efficiency can be increased. Furthermore, since at the time of measurement the arrangement of chemical materials can be handled with certainty along a one-dimensional route, the reliability of measurement is high. An example of a narrow and long member with flexibility includes, for example, those that are formed by chemical fibers, such as nylon.

Moreover, the configuration elements above, such as the carriers, the narrow tubes, the tip form vessel, the nozzle head, the sealing section, and the nozzle, as well as the heating device or the like, and the devices, can be arbitrarily combined while making suitable changes. Furthermore, the ligand is not restricted to DNA, and it includes genetic material such as oligonucleotides and RNA, immunity materials, proteins, sugar chains, and further includes pheromones, allomones, mitochondria, viruses, and plasmids.

Furthermore, the aforementioned reagents and materials show examples, and it is also possible to utilize other reagents and materials. Moreover, a carrier in which DNA, or the like, has been collected can be taken out from the narrow tube, or the like, and it can be made the subject of preservation, or other processes.

INDUSTRIAL APPLICABILITY

The present invention relates to a biological material fixed carrier enclosing tip, a biological material fixed carrier treatment apparatus and a method thereof. The present invention relates to all fields, such as fields in which handling of biopolymers, such as genes, the immune system, amino acids, proteins, and sugars, and biological low molecular weight compounds is demanded, for example, in agricultural fields such as engineering fields, food products, agricultural produce and seafood processing, medical fields such as pharmacology fields, sanitation, immunity, diseases, and genetics, and science fields such as chemistry or biology. The present invention is, in particular, an effective method in cases where a series of processes using a plurality of reagents and materials is continuously executed in a predetermined order.

BRIEF DESCRIPTION OF THE REFERENCE SYMBOLS

10 Biological material fixed carrier treatment apparatus
11, 25, 35, 47, 56, 58, 62, 65, 68, 70 Biological material fixed carrier enclosing tip
12, 36, 48 Tip form vessel
13, 37, 49 Wide tube
15, 39, 51 Narrow tube
17, 26, 41, 59, 63, 66, 69 Carrier
18, 19, 28, 27, 43, 61, 64, 67 Enclosing section
84 Collective nozzle head
84' Individual nozzle head
103 Conveyor (queued route transporting device)
106 Light receiving section
184 Nozzle head

The invention claimed is:

1. A biological material fixed carrier enclosing tip comprising:
a tip form vessel having an installation opening part that is installable to a nozzle that performs suction and discharge of gas, and a narrow tube that is insertable into various vessels and possesses an opening, through which fluid inflow and outflow is possible by means of said suction and discharge of gas, that is narrower than said nozzle;
a carrier in which a predetermined biological material is fixed or fixable in a plurality of different positions that are determined beforehand that are distinguishable from the exterior, and has a size or a shape that is able to pass through said opening; and
an enclosing section provided on said tip form vessel that encloses the carrier within the narrow tube in a state where it is able to make contact with the fluid that has flown into said narrow tube from said opening,
wherein said tip form vessel has a storage section that communicates said installation opening part and the narrow tube, in which liquid is storable,
wherein said narrow tube is provided with respect to said storage section, as a separate body, such that the upper side of the narrow tube is provided with respect to an engage section of said storage section,
wherein said carrier has a plurality of particle form carriers,
wherein said enclosing section is provided such that it sandwiches said plurality of particle form carriers at two adjacent positions within the narrow tube in a state where the particle form carriers are trapped along the direction of fluid inflow and outflow and are serially arranged such that the order thereof becomes constant within the narrow tube, and the plurality of different positions determined beforehand are made to correspond to said plurality of particle form carriers that are arranged in a predetermined order,
wherein said enclosing section has a first carrier passage blocking member and a second carrier passage blocking member such that an interval between the first carrier passage blocking member and the second carrier passage blocking member is greater than the length of the plurality of particle form carriers,
wherein the first carrier passage blocking member protrudes radially inwardly from an inner wall face of said tip form vessel to block the plurality of particle form carriers from exiting the opening of the narrow tube while permitting relative movement between the plurality of particle form carriers and the first carrier passage blocking member,
wherein the first carrier passage blocking member is entirely within the narrow tube so that at least a portion of the narrow tube extends between the first carrier passage blocking member and the opening of the narrow tube, and
wherein an inner diameter of the narrow tube is greater than an outer diameter of the plurality of particle form carriers and less than twice the outer diameter of the plurality of particle form carriers.

2. A biological material fixed carrier enclosing tip according to claim 1, wherein the first carrier passage blocking members is provided as a separate body with respect to the tip form vessel, such that an interval between said installation opening part and said opening is partitioned, such that fluid is able to pass through, but said carrier is not able to pass through.

3. A biological material solid body enclosing tip according to claim 1, wherein the inner wall face of said tip form vessel forms the first carrier passage blocking member.

4. A biological material fixed carrier enclosing tip according to claim 1, in which the entire wall of said tip form vessel, or a portion thereof, is formed by a conductive member that has a predetermined electrical resistance value.

5. A biological material fixed carrier enclosing tip according to claim 1, wherein a particle form carrier arranged at, at the very least, one end within said plurality of particle form carriers, has concavities and convexities on the surface thereof.

6. A biological material fixed carrier enclosing tip according to claim 1, wherein within the narrow tube in which said carrier is enclosed, the capacity of the space in which fluid is storable is approximately several microliters to several hundred microliters.

7. A biological material fixed carrier enclosing tip comprising:
a tip form vessel having an installation opening part that is installable to a nozzle that performs suction and discharge of gas, and a narrow tube that is insertable into various vessels and possesses an opening, through which fluid inflow and outflow is possible by means of said suction and discharge of gas, that is narrower than said nozzle;
a carrier in which a predetermined biological material is fixed or fixable in a plurality of different positions that are determined beforehand that are distinguishable from the exterior, and has a size or a shape that is able to pass through said opening; and
an enclosing section provided on said tip form vessel that encloses the carrier within the narrow tube in a state where it is able to make contact with the fluid that has flown into said narrow tube from said opening,
wherein said tip form vessel has a storage section that communicates said installation opening part and the narrow tube, in which liquid is storable,
wherein said narrow tube is provided with respect to said storage section, as a separate body, such that the upper side of the narrow tube is provided with respect to an engage section of said storage section,
wherein said carrier is a narrow and long shaped linear form flexible, and the predetermined biological material is fixed or is fixable along the longitudinal direction of the linear form flexible carrier at positions determined beforehand that are identifiable from the exterior,
wherein said enclosing section has a joining section which joins the linear form flexible carrier to said narrow tube at two points thereof along the longitudinal direction of said linear form flexible carrier, which are separated by a predetermined distance, such that said fluid is passable, and
wherein the linear form flexible carrier is selected from the group consisting of:
a thread form carrier that linearly extends along a central axis of the narrow tube such that the linear form flexible carrier is separated from an inner wall face of the narrow tube; and
a string form carrier that linearly extends along the central axis of the narrow tube such that the linear form flexible carrier is separated from the inner wall face of the narrow tube.

8. A biological material fixed carrier enclosing tip comprising:
a tip form vessel having an installation opening part that is installable to a nozzle that performs suction and discharge of gas, and a narrow tube that is insertable into various vessels and possesses an opening, through which fluid inflow and outflow is possible by means of said suction and discharge of gas, that is narrower than said nozzle;
a carrier in which a predetermined biological material is fixed or fixable in a plurality of different positions that are determined beforehand that are distinguishable from the exterior, and has a size or a shape that is able to pass through said opening; and
an enclosing section provided on said tip form vessel that encloses the carrier within the narrow tube in a state where it is able to make contact with the fluid that has flown into said narrow tube from said opening,
wherein said tip form vessel has a storage section that communicates said installation opening part and the narrow tube, in which liquid is storable,
wherein said narrow tube is provided with respect to said storage section, as a separate body, such that the upper side of the narrow tube is provided with respect to an engage section of said storage section,
wherein said carrier is a non-flexible narrow and long shaped linear form non-flexible carrier having a first end and an opposing second end, the predetermined biological material is fixed or is fixable along the longitudinal direction of said linear form non-flexible carrier at positions determined beforehand that are identifiable from the exterior,
wherein said enclosing section has a joining section which joins the linear form non-flexible carrier to said narrow tube at only one location thereof such that said fluid is passable and such that only the first end of the linear form non-flexible carrier is fixed to the joining section and the second end of the linear form non-flexible carrier is free and thus not fixed to the joining section, and
wherein the linear form non-flexible carrier is selected from the group consisting of:
a wire form carrier that linearly extends along a central axis of the narrow tube such that the wire form carrier is separated from an inner wall face of the narrow tube; and
a rod form carrier that linearly extends along the central axis of the narrow tube such that the rod form carrier is separated from the inner wall face of the narrow tube.

9. A biological material fixed carrier treatment apparatus comprising:
a nozzle head that has one or a plurality of consecutive nozzles that perform suction and discharge of gas;
a suction and discharge mechanism that performs suction and discharge of gas via the nozzles;
a tip form vessel having an installation opening part that is installed to said nozzle, and a narrow tube that is insertable into various vessels and possesses an opening, through which fluid inflow and outflow is possible by means of said suction and discharge of gas, that is narrower than said nozzle;
one or two or more biological material fixed carrier enclosing tips having an enclosing section that encloses a carrier in which a predetermined biological material is fixed or fixable in a plurality of different positions that are determined beforehand that are distinguishable from the exterior, and that has a size or a shape that is able to pass through said opening; and that is provided on said tip form vessel that encloses the carrier within the narrow tube in a state where it is able to make contact with the fluid that has flown into said narrow tube from said opening, and in which said tip form vessel has a storage section that communicates said installation opening part and the narrow tube, in which liquid is storable,
a stage to which a liquid storage section group, in which a variety of liquids are stored or are storable, is provided;
a movement device that relatively and horizontally moves said nozzle head with respect to said liquid storage section group; and
a control section that controls the amount, the speed, the frequency, the time, or the position of the suction and discharge of said nozzles based on; the structure of said biological material fixed carrier enclosing tip, the material conditions comprising the type of biological material that is fixed to the carrier or is present within the fluid, the concentration, the amount of liquid, and the coordinate position containing the storage position of the liquid, and the processing contents, and controls the temperature control based on the processing contents, wherein a temperature raising and lowering body, which raises and lowers the temperature of said narrow tube as a result of a signal from the exterior, is able to be in the vicinity of or making contact with, the outside of said narrow tube of said biological material fixed carrier enclosing tip installed to the nozzle by a horizontal movement of the temperature raising and lowering body with respect to said biological material fixed carrier enclosing tip installed to the nozzle, so as to perform temperature control on the carrier enclosed in the narrow tube of said biological material fixed carrier enclosing tip, wherein the temperature raising and lowering body is provided on a chassis to which the nozzle head is coupled, and wherein the nozzles are vertically movable with respect to the chassis.

10. A biological material fixed carrier treatment apparatus according to claim 9, further comprising a light reception device that receives light from said carrier stored within said tip form vessel.

11. A biological material fixed carrier treatment apparatus according to claim 9, wherein the capacity of a space in which liquid is storable within a narrow tube, in which said carrier is enclosed, is approximately several microliters to several hundred microliters.

12. A biological material fixed carrier treatment apparatus according to claim 9, wherein said nozzle head has a collective nozzle head in which a plurality of consecutive nozzles are arranged along the column direction and an individual nozzle head that has at least one nozzle, said suction and discharge mechanism has a collective suction and discharge mechanism that simultaneously performs suction and discharge of gas with respect to the plurality of consecutive nozzles of said collective nozzle head, and an individual suction and discharge mechanism that individually performs suction and discharge of gas with respect to each nozzle of said individual nozzle head, and said movement device has, a nozzle head movement device that relatively moves said collective nozzle head and said individual nozzle head in said row direction with respect to said liquid storage section group, and a transporting route that includes a column transporting route that is on the movement route of said collective nozzle head and along said column direction and a row transporting route that is on the movement route of said individual nozzle head and along said row direction, and has a queued route transporting device that transports a transport storage section, in which tips that have been detached from said collective nozzle head or liquid that has been discharged from said collective nozzle head are respectively storable, along said transporting route.

13. A biological material fixed carrier treatment apparatus according to claim 12, wherein a light reception device, which receives light from said transport storage section, is provided at a predetermined position along said transporting route of said queued route transporting device.

14. A biological material fixed carrier treatment apparatus according to claim 9, wherein said nozzle head has a plurality of consecutive collective nozzles and one individual nozzle arranged along the column direction, said suction and discharge mechanism simultaneously performs suction and discharge of gas with respect to the collective nozzles and the individual nozzle of said nozzle head, and said movement device has, a nozzle head movement device that relatively moves said nozzle head along the row direction with respect to a stage that has said liquid storage section group, and a transporting route that includes a column transporting route that is on the movement route of said collective nozzles and along said column direction and a row transporting route that is on the movement route of said individual nozzle and along said row direction, and has a queued route transporting device that transports a transport storage section, in which tip form vessels that have been detached from said collective nozzle or liquid that has been discharged from said collective nozzle head are respectively storable, along said transporting route.

15. A biological material fixed carrier treatment apparatus according to claim 14, wherein a light reception device, which receives light from said transport storage section, is provided at a predetermined position along said transporting route of said queued route transporting device.

16. A biological material fixed carrier treatment method comprising:

a fixing step for fixing a predetermined biological material to a carrier such that it is associated with a predetermined position by a predetermined relationship;

an enclosing step for storing said carrier, to which said biological material is fixed within a tip form vessel which has an installation opening part that is installable to one or a plurality of consecutive nozzles that perform suction and discharge of gas, and a narrow tube that has an opening, through which inflow and outflow of fluid is possible by means of the suction and discharge of gas, and is narrower than said nozzle, and moreover that has a storage section that communicates said installation opening part and the narrow tube, in which liquid is storable, and enclosing the carrier within said narrow tube in a state where it is able to make contact with the fluid that has flowed in from said opening to within the vessel by using an enclosing section, attaching said narrow tube to said storage section, and installing to said nozzle at the installation opening part of the vessel; and a reaction step for moving a nozzle to which said tip form vessel has been installed to a predetermined liquid storage section by a horizontal movement of the nozzle with respect to the liquid storage section and a vertical movement of the nozzle with respect to a chassis to which the nozzle is coupled, and bringing into contact and reacting the biological material fixed to said carrier and a solution stored in the liquid storage section by controlling the operation of suction and discharge, which comprises the amount of suction and discharge via said nozzle, the speed, the frequency, the time, or the location, based on the structure of the tip form vessel, the material conditions comprising the type of biological material that is fixed to the carrier or is present in the solution, the concentration, the amount of solution, or the position coordinates which includes the storage position of the solution, and the processing contents, and the temperature control, based on the processing contents, wherein at the reaction step, the temperature of said narrow tube is raised or lowered as a result of a signal from the exterior by providing a temperature raising and lowering body that is coupled to the chassis so as to be able to be in the vicinity of or making contact with, the outside of said narrow tube installed to said nozzle by a horizontal movement of the temperature raising and lowering body with respect to said narrow tube installed to the nozzle, so as to perform temperature control on the carrier enclosed in the narrow tube of the tip form vessel that is vertically movable with respect to the chassis.

17. A biological material fixed carrier treatment method according to claim 16, that, following said reaction step, has a light reception step for receiving light from said carrier stored within said tip form vessel.

18. A biological material fixed carrier treatment method according to claim 16, wherein
said carrier has a plurality of particle form carriers,
said enclosing step includes a step for cleaning the plurality of particle form carriers by using a suitable solvent, and
said reaction step has a step for cleaning said plurality of particle form carriers by performing suction and discharge of a cleaning solution from said liquid storage section, in which a cleaning solution is stored, at a predetermined speed and frequency.

* * * * *